United States Patent
Song et al.

(10) Patent No.: US 6,660,755 B2
(45) Date of Patent: Dec. 9, 2003

(54) SUBSTITUTED DIARYL OR DIHETEROARYL METHANS, ETHERS AND AMINES HAVING RETINOID AGONIST, ANTAGONIST OR INVERSE AGONIST TYPE BIOLOGICAL ACTIVITY

(75) Inventors: Tae K. Song, Long Beach, CA (US); Min Teng, Aliso Viejo, CA (US); Roshantha A. Chandraratna, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 15 days.

(21) Appl. No.: 10/212,386

(22) Filed: Aug. 5, 2002

(65) Prior Publication Data

US 2003/0109687 A1 Jun. 12, 2003

Related U.S. Application Data

(62) Division of application No. 09/708,972, filed on Nov. 8, 2000, now Pat. No. 6,455,701, which is a division of application No. 09/267,992, filed on Mar. 12, 1999, now Pat. No. 6,187,950, which is a division of application No. 08/840,040, filed on Apr. 24, 1997, now Pat. No. 5,919,970.

(51) Int. Cl.$^7$ ............. A61K 31/192; A61K 31/235
(52) U.S. Cl. ............. 514/354; 514/356; 514/534; 514/544; 514/567; 514/568
(58) Field of Search ............. 514/354, 356, 514/534, 544, 567, 568

(56) References Cited

U.S. PATENT DOCUMENTS

| | | | |
|---|---|---|---|
| 4,096,341 A | 6/1978 | Frazer | 514/345 |
| 4,326,055 A | 4/1982 | Loeliger | |
| 4,391,731 A | 7/1983 | Boller et al. | 252/299.26 |
| 4,539,154 A | 9/1985 | Krebs | 260/410 |
| 4,695,649 A | 9/1987 | Magami et al. | 514/437 |
| 4,723,028 A | 2/1988 | Shudo | |
| 4,739,098 A | 4/1988 | Chandraratna | 549/23 |
| 4,740,519 A | 4/1988 | Shroot et al. | 514/337 |
| 4,810,804 A | 3/1989 | Chandraratna | 549/398 |
| 4,826,969 A | 5/1989 | Maignan et al. | 514/233 |
| 4,826,984 A | 5/1989 | Berlin et al. | 546/134 |
| 4,855,320 A | 8/1989 | Chatterjee et al. | 514/337 |
| 4,895,868 A | 1/1990 | Chandraratna | 560/8 |
| 4,923,884 A | 5/1990 | Chandraratna | 514/354 |
| 4,927,947 A | 5/1990 | Chandraratna | 549/484 |
| 4,980,369 A | 12/1990 | Chandraratna | 542/429 |
| 4,992,468 A | 2/1991 | Chandraratna | 514/510 |
| 5,006,550 A | 4/1991 | Chandraratna | 514/465 |
| 5,013,744 A | 5/1991 | Chandraratna | |
| 5,015,658 A | 5/1991 | Chandraratna | |
| 5,023,341 A | 6/1991 | Chandraratna | |
| 5,037,825 A | 8/1991 | Klaus et al. | 514/233.8 |
| 5,045,551 A | 9/1991 | Chandraratna | |
| 5,053,523 A | 10/1991 | Chandraratna | |
| 5,068,252 A | 11/1991 | Chandraratna | |
| 5,089,509 A | 2/1992 | Chandraratna | |
| 5,130,335 A | 7/1992 | Chandraratna | |
| 5,134,159 A | 7/1992 | Chandraratna | |
| 5,162,546 A | 11/1992 | Chandraratna | 549/23 |
| 5,175,185 A | 12/1992 | Chandraratna | 514/445 |
| 5,183,827 A | 2/1993 | Chandraratna | 514/444 |
| 5,202,471 A | 4/1993 | Chandraratna | 562/473 |
| 5,231,113 A | 7/1993 | Chandraratna | 514/510 |
| 5,234,926 A | 8/1993 | Chandraratna | 514/253 |
| 5,248,777 A | 9/1993 | Chandraratna | 546/165 |
| 5,264,456 A | 11/1993 | Chandraratna | 514/461 |
| 5,264,578 A | 11/1993 | Chandraratna | 546/269 |
| 5,272,156 A | 12/1993 | Chandraratna | 514/314 |
| 5,278,318 A | 1/1994 | Chandraratna | 549/23 |
| 5,324,744 A | 6/1994 | Chandraratna | 514/456 |
| 5,324,840 A | 6/1994 | Chandraratna | 546/318 |
| 5,326,898 A | 7/1994 | Chandraratna | 560/17 |
| 5,344,959 A | 9/1994 | Chandraratna | 560/100 |
| 5,346,895 A | 9/1994 | Chandraratna | 514/247 |
| 5,346,915 A | 9/1994 | Chandraratna | 514/432 |
| 5,348,972 A | 9/1994 | Chandraratna | 514/432 |
| 5,348,975 A | 9/1994 | Chandraratna | 514/456 |
| 5,349,105 A | 9/1994 | Chandraratna | 564/163 |
| 5,354,752 A | 10/1994 | Chandraratna | 514/252 |
| 5,354,776 A | 10/1994 | Chandraratna | 514/461 |
| 5,380,877 A | 1/1995 | Chandraratna | 549/60 |
| 5,391,753 A | 2/1995 | Chandraratna | 546/323 |
| 5,399,561 A | 3/1995 | Chandraratna | 514/252 |
| 5,399,586 A | 3/1995 | Davies et al. | 514/448 |
| 5,407,937 A | 4/1995 | Chandraratna | 514/256 |
| 5,414,007 A | 5/1995 | Chandraratna | 514/365 |
| 5,420,145 A | 5/1995 | Shudo | 514/352 |
| 5,426,118 A | 6/1995 | Chandraratna | 514/337 |
| 5,434,173 A | 7/1995 | Chandraratna | 514/354 |

(List continued on next page.)

FOREIGN PATENT DOCUMENTS

| | | |
|---|---|---|
| DE | 3316932 | 11/1983 |
| DE | 3524199 | 1/1986 |
| DE | 3602473 | 7/1987 |

(List continued on next page.)

OTHER PUBLICATIONS

A. General Synthesis of Terminal and Internal Arylalkynes by the Palladium–Catalyzed Reaction of Alkynylzinc Reagents with aryl Halides by Anthony O. King and Ei–ichi, Negishi, *J. Org. Chem.*, (1978) 43/2: p. 358.

Conversion of Methyl Ketones into Terminal Acetylenes and (E)–Tri-substituted Olefins of Terpenoid Origin by Ei–ichi, et al., *J. Org. Chem.*, (1980) 45/12: p. 2526.

(List continued on next page.)

Primary Examiner—Richard L. Raymond
(74) Attorney, Agent, or Firm—Gabor L. Szekeres; Robert J. Baran; Martin A. Voet

(57) ABSTRACT

Compounds of the formula

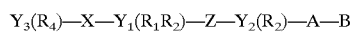

where the symbols have the meaning defined in the specification, have retinoid, retinoid antagonist or retinoid inverse agonist type biological activity.

10 Claims, No Drawings

U.S. PATENT DOCUMENTS

| | | | |
|---|---|---|---|
| 5,451,605 A | 9/1995 | Chandraratna et al. | 514/475 |
| 5,455,265 A | 10/1995 | Chandraratna | 514/448 |
| 5,466,861 A | 11/1995 | Dawson et al. | 560/100 |
| 5,468,879 A | 11/1995 | Chandraratna | 549/23 |
| 5,470,999 A | 11/1995 | Chandraratna | 560/100 |
| 5,475,022 A | 12/1995 | Chandraratna | 514/448 |
| 5,475,113 A | 12/1995 | Chandraratna | 548/203 |
| 5,489,584 A | 2/1996 | Vuligonda et al. | 514/188 |
| 5,498,755 A | 3/1996 | Chandraratna et al. | 564/272 |
| 5,498,795 A | 3/1996 | Song et al. | 562/474 |
| 5,514,825 A | 5/1996 | Vuligonda et al. | 558/462 |
| 5,516,904 A | 5/1996 | Chandraratna | 514/269 |
| 5,523,457 A | 6/1996 | Starrett, Jr. et al. | 560/24 |
| 5,534,516 A | 7/1996 | Chandraratna | 514/253 |
| 5,534,641 A | 7/1996 | Song et al. | 549/416 |
| 5,543,534 A | 8/1996 | Vuligonda et al. | 549/421 |
| 5,556,996 A | 9/1996 | Beard et al. | 549/407 |
| 5,559,248 A | 9/1996 | Starrett, Jr. et al. | 549/79 |
| 5,563,292 A | 10/1996 | Shih et al. | 560/255 |
| 5,591,858 A | 1/1997 | Vuligonda et al. | 546/322 |
| 5,599,819 A | 2/1997 | Chandraratna | 514/354 |
| 5,599,967 A | 2/1997 | Vuligonda et al. | 560/48 |
| 5,602,130 A | 2/1997 | Chandraratna | 514/247 |
| 5,602,135 A | 2/1997 | Chandraratna | 514/252 |
| 5,605,915 A | 2/1997 | Vuligonda et al. | 514/356 |
| 5,616,597 A | 4/1997 | Chandraratna | 514/365 |
| 5,616,712 A | 4/1997 | Teng et al. | 546/158 |
| 5,618,836 A | 4/1997 | Chandraratna et al. | 514/444 |
| 5,618,931 A | 4/1997 | Beard et al. | 544/224 |
| 5,618,943 A | 4/1997 | Vuligonda et al. | 546/342 |
| 5,648,503 A | 7/1997 | Vuligonda et al. | 549/13 |
| 5,648,514 A | 7/1997 | Johnson et al. | 560/102 |
| 5,654,469 A | 8/1997 | Vuligonda et al. | 560/56 |
| 5,663,347 A | 9/1997 | Chandraratna | 546/152 |
| 5,663,357 A | 9/1997 | Teng et al. | 546/323 |
| 5,663,367 A | 9/1997 | Vuligonda et al. | 549/4 |

FOREIGN PATENT DOCUMENTS

| | | |
|---|---|---|
| DE | 3708060 | 9/1987 |
| DE | 3715955 | 11/1987 |
| EP | 0098591 | 1/1984 |
| EP | 0130795 | 1/1985 |
| EP | 170105 A | 2/1986 |
| EP | 0176032 | 4/1986 |
| EP | 0176033 | 4/1986 |
| EP | 0253302 | 1/1988 |
| EP | 0272921 | 6/1988 |
| EP | 0284261 | 9/1988 |
| EP | 0284288 | 9/1988 |
| EP | 0286364 | 10/1988 |
| EP | 0303186 | 2/1989 |
| EP | 0303915 | 2/1989 |
| EP | 176034 A | 4/1989 |
| EP | 0315071 | 5/1989 |
| EP | 0350846 | 7/1989 |
| EP | 0412387 | 2/1991 |
| EP | 0478787 | 10/1991 |
| EP | 0514269 | 11/1992 |
| EP | 0617020 | 9/1994 |
| EP | 0619116 | 10/1994 |
| EP | 0661259 | 5/1995 |
| EP | 0661258 | 7/1995 |
| EP | 0661261 | 7/1995 |
| EP | 0718285 | 8/1996 |
| GB | 2190378 | 11/1983 |
| WO | 85/00806 | 2/1985 |
| WO | 85/04652 | 10/1985 |
| WO | 91/16051 | 10/1991 |
| WO | 92/06948 | 4/1992 |
| WO | 93/03713 | 3/1993 |
| WO | 93/11755 | 6/1993 |
| WO | 93/21146 | 10/1993 |
| WO | 94/14777 | 7/1994 |
| WO | 95/04036 | 2/1995 |
| WO | 96/05165 | 2/1996 |

OTHER PUBLICATIONS

Sporn et al., in *J. Amer. Acad. Derm..*, (1986) 15:756–764.

"A Convenient Synthesis of Ethynylarenes and Diethynylarenes" by S. Takahashi et al. *Synthesis* (1980) p. 627–630.

Shudo et al., in *Chem. Phar. Bull.*, (1985) 33:404–407.

Kagechika et al., in *J. Med. Chem.*, (1988) 31:2182–2192.

Chemistry and Biology of Synthetic Retinoids by Marcia I. Dawson and William H. Okamura, published by CRC Press Inc., 1990, p. 334–335, 354.

Synthesis of 2,2'–Diacyl–1,1'–Biaryls. Regiocontrolled Protection of . . . by Mervic, et al, *J. Org. Chem.*, (1980) No. 45, p. 4720–4725.

A Dopamine Receptor Model and Its Application in the Design of a New Class of Regid Pyrrolo[2,3–g]isoquinoline Antipsychotics, Gary L. Olson et al. *American Chemical Societe*, (1981) 24/9:1026–1031.

6.2.3 Conformational Restriction, Williams, et al., *Drug Discovery and Development*, The Humana Press, (1987) pp. 54–55.

V. Retinoid Structure–Biological Activity Relationships, Chemistry And Biology of Synthetic Retinoids, (1990) pp. 324–356.

Davis et al. *J. Organomettalic Chem* (1990) 387:381–390.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Galnds: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3:.

"Synthesis and Evaluation of Stilbene and Dihydrostilbene Derivateives as Potential Anticancer Agents That Inhibit Tubulin Polymerization" by Cushman, Mark et al *J. Med. Chem.*, (1991), 34:2579–2588.

"Synthesis and Evaluatinof New Pretoein Tyrosine Kinase Inhibitors. Part 1. Pyridine– Containing Stilbenes and Amides" by Cushman, Mark et al. *Bioorganic & Medicinal Chemistry Letters*, (1991) 1/4:211–214.

"Di– and Tri–methoxystyryl Derivatives of Heterocyclic Nitrogen Compounds" by Bahner, C. T. et al. *Arzneim–Forsch,/Drug Res*, (1981)31 (I), Nr. 3.

"Retinobenzoic acids. 3. Structure–Activity Relationships of Retinoidal Azobenzene–4– Carboxylic Acids and Stilbene–4– Carboxylic Acids" by H. Kagechika et al., *Journal of Medicinal Chemistry*, (1989), 31:1098–1108.

Eyrolles, L. et al. "Retinoid Antagonists: Molecular Design Based on the Ligand Superfamily Concept" *Med. Chem. Res.*, (1992) 2:361–367.

Liu, S. S. et al. "Systemic Pharmacokinetics of Acetylenic Retinoids in Rats", *Drug Metabolism and Disposition*, (1990) 18/6: 1071–1077.

Chemical Abstracts, vol. 122, No. 13,Mar. 27, 1995 abstract No. 151372m, (S. Kaku et al.).

Chemical Abstracts, vol. 117, No. 13, Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, Aug. 2, 1996, pp. 3035–3038, Min Teng et al.

Journal of Medicinal Chemistry, vol. 37, No. 10, May 13,1994, pp. 1508–1517, Laurence Eyrolles.

Biochemical and Biophysical Research communications, vol. 155 No. 1, 1988, pp. 503–508.

Chemical Abstracts. vol. 121, No. 9, 1994.

Database WPi, Section CH, Week 9416, Derwent Publication Ltd. London, GB; AN 94–128759 and JP 6078266A, see English Language abstract in Derwent.

Journal of Medicinal Chemistry, vol. 38, No. 16, Aug. 4, 1995, pp. 3163–3173.

Weiner, et al., "A Phase I trial of topically applied trans – retinoic acid in cervical dysplasia– clinical efficacy", *Investigational New Drugs*, 4:241–244, 1996.

Jones, et al., "A dose–response study of 13–cis–retinoic acid in acne vulgaris", *British Jornal of Dermatology*, (1983) 108, 333–343.

Fekrat, et al., "The Effect of Oral 13–cis–retinoic Acid on Retinal Redetachment after Surgical Repair in Eyes with Proliferative Vitreoretinopathy", *Ophthalmology*, vol. 102, No. 3 (Mar. 1995), pp. 412–418.

Nagpal, et al., "Separation of Transactivation and AP1 Antagonism Functions of Retinoic Acid Receptor $\alpha$*", *The Journal of Biological Chemistry*, 270/2(1995): 923–927.

Allegretto, et al., "Transactivation Properties of Retinoic Acid and Retinoid X Receptors in Mammalian Cells and Yeast", *The Journal of Biological Chemistry*, vol. 268, No. 35 (Dec. 15, 1993), pp. 26625–26633.

Gruapner, et al., "6'–Substituted Naphthalene–2–Carboxylic Acid Analogs, A new Class of Retinoic Acid Receptor Sybtype–Specific Ligands," *Biochemical and Biophysical Research Communications*, vol. 179, No. 3 (Sep. 30, 1991), pp. 1554–1561.

Moore, et al., "Retinoic Acid and Interferon in Human Cancer: Mechanisms and Clinical Studies," *Seminars in Hematology*, 31/4, Suppl 5 (Oct. 1994), pp. 31–37.

Isozaki et al., (CA 128:371, JP 09268125) 1998.

Isozaki et al. (CA 126:74552, JP 08291127) 1997.

Ogawa Tadashi, (CA 125:260761, JP 08184865) 1996.

SUBSTITUTED DIARYL OR DIHETEROARYL METHANS, ETHERS AND AMINES HAVING RETINOID AGONIST, ANTAGONIST OR INVERSE AGONIST TYPE BIOLOGICAL ACTIVITY

CROSS-REFERENCE TO RELATED APPLICATION

The present application is a divisional of application Ser. No. 09/708,972, filed on Nov. 8, 2000 now U.S. Pat. No. 6,455,701, which is a divisional of application Ser. No. 09/267,992, filed on Mar. 12, 1999, now U.S. Pat. No. 6,187,950, which is a divisional of application Ser. No. 08/840,040, filed on Apr. 24, 1997, now U.S. Pat. No. 5,919,970.

BACKGROUND OF THE INVENTION

1. Field of the Invention

The present invention relates to novel compounds having retinoid-like, retinoid antagonist and/or retinoid inverse-agonist-like biological activity. More specifically, the present invention relates to substituted diaryl or diheteroaryl methane, ether and amine derivatives which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Several United States Patents assigned to the same assignee as the present application and patents and publications cited therein describe or relate to substituted phenyl derivatives having retinoid like biological activity. Examples of such patents are: 4,980,369; 4,992,468; 5,006,550; 5,013,744; 5,015,658; 5,068,252; 5,130,355; 5,134,159; 5,162,546; 5,202,471; 5,231,113; 5,278,318; 5,324,744; 5,324;840; 5,326,898; 5,346,915; 5,348,975; 5,349,105; 5,391,753; 5,414,007; 5,434,173; 5,498,755; 5,498,795; 5,534,641, and 5,556,996. Still further, several co-pending applications and recently issued patents which are assigned to the assignee of the present application, are directed to further compounds having retinoid-like activity.

Although pharmaceutical compositions containing retinoids have well established utility (as is demonstrated by the foregoing citation of patents and publications from the voluminous literature devoted to this subject) retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXB_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist), the compound may elicit an agonist-like response on all receptor subtypes (pan-agonist), or a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists.

It has been recently discovered and described in pending applications assigned to the same assignee as the present application that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well. More particularly, regarding the published scientific and patent literature in this field, published PCT application WO 94/14777 describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. J. Med. Chem. 1995, 38, 3163–3173. Kaneko et al. Med. Chem Res. 1991, 1:220–225; Apfel et al. Proc. Natl. Acad. Sci. USA 89 7129–7133 August 1992 Cell Biology; Eckhardt et al. Toxicology Letters 1994, 70, 299–308; Keidel et al. Molecular and Cellular Biology, 1994, 14, 287–298; and Eyrolles et al J. Med. Chem. 1994, 37, 1508–1517 describe compounds which have antagonist like activity at one or more of the RAR retinoid subtypes.

SUMMARY OF THE INVENTION

The present invention relates to compounds of Formula 1

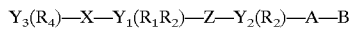

Formula 1 where $Y_1$ is phenyl, naphthyl or heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being substituted with an $R_1$ group, and further substituted or unsubstituted with one or two $R_2$ groups;

$R_1$ is $C_{1-10}$alkyl, 1-adamantyl, 2-tetrahydropyranoxy, trialkylsilanyloxy where alkyl has up to 6 carbons, OH, alkoxy where the alkyl group has up to 10 carbons, alkylthio where the alkyl group has up to 10 carbons, or $OCH_2OC_{1-6}$alkyl;

$R_2$ is lower alkyl of 1 to 6 carbons, F, Cl, Br, I, $CF_3$, $CF_2CF_3$, OH, $OR_3$, $NO_2$, $N(R_3)_2$, CN, $N_3$, $COR_3$, or $NHCOR_3$, COOH, $COOR_3$;

X is $C(R_3)_2$, S, SO, $SO_2$, O or $NR_3$;

Z is —C≡C—,
—N=N—,
—N(O)=N—,
—N=N(O)—,
—N=CR_3—,
—CR_3=N,
—(CR_3=CR_3)_n— wherein is an integer having the value 0-5,
—CO—NR_3—,
—CS—NR_3—,
—NR_3—CO,
—NR_3—CS,
—COO—,
—OCO—;
—CSO—;
—OCS—;
—CO—CR_3=CR_3—;

$R_3$ is independently H or lower alkyl of 1 to 6 carbons;

$Y_2$ is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being unsubstituted or substituted with one or two $R_2$ groups, or when Z is —$(CR_3=CR_3)_n$ and n is 3, 4 or 5 then $Y_2$ represents a direct valence bond between said $(CR_3=CR_3)_n$ group and B;

$Y_3$ is phenyl, naphthyl or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one to three $R_4$ groups, where $R_4$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, $NR_3$, $N_3$, COOH, $COOC_{1-6}$alkyl; OH, SH, $OC_{1-6}$alkyl, $SC_{1-6}$alkyl;

A is $(CH_2)_q$ where q is 0-5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CH(OR_{13}O)$, —$COR_7$, $CR_7(OR_{12})_2$, $CR_7(OR_{13}O)$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

Biological Activity, Modes of Administration
Assays of Retinoid-Like or Retinoid Antagonist and Inverse Agonist-Like Biological Activity A classic measure of retinoic acid activity involves measuring the effects of retinoic acid on ornithine decarboxylase. The original work on the correlation between retinoic acid and decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Research 1975, 35, 1662–1670 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\Gamma$ receptors, and the ability or inability of the compounds to activate transcription of a reporter gene through these receptor subtypes can be tested.

Specifically, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M (1989) Focus, 112 is described in detail in U.S. Pat. No. 5,455,265 the specification of which is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 1992, 68, 397–406; Allegretto et al. J. Biol. Chem. 1993 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology 22, 3099–3108, expressly incorporated herein by reference.) Still another transactivation assay, the "PGR assay" is described in the publication Klein et al. J. Biol. Chem. 1996, 271, 22692–22696, which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4\times10^5$ cells/well) were transiently transfected with the luciferase reporter plasmid MTV-4(R5G)-Luc (0.7 μg/well) containing four copies of the R5G retinoid DNA response element along with the RXRα expression plasmid pRS-hRXRa (0.1 μg/well) and one of the RAR-P-GR expression plasmids (0.05 μg/well) in 12 well plates via calcium phosphate precipitation Chen et al. Mol. Cell. Biol. 1987, 7, 2745–2752 as described by Klein et al. J. Biol. Chem. 1996, 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 μg/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 Al) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet Mol. Cell. Biol. 1987, 7, 725–737. Luciferase values represent the mean±SEM of triplicate determinations normalized to β-galactosidase activity. The results of the PGR assay are also expressed in $EC_{50}$ numbers (nanomolar concentration).

Table 1 below shows the results of the PGR assay for certain exemplary compounds of the invention for the receptor subtypes in the RAR group and Table 2 shows the results of the ligand binding assay for the same compounds. As it can be seen from the Tables, these exemplary compounds do not transactivate but bind to the receptor and therefore have retinoid antagonist (or inverse agonist) effects.

TABLE 1

PGR Assay Data (transactivation)

| | $EC_{50}$ (nanomolar) | | | % Efficiency[1] | | |
|---|---|---|---|---|---|---|
| Compound No. | $RAR_\alpha$ | $RAR_\beta$ | $RAR_\gamma$ | $RAR_\alpha$ | $RAR_\beta$ | $RAR_\gamma$ |
| 6 | $NA^2$ | NA | NA | 0 | 0 | 70 |
| 10 | NA | NA | NA | 0 | 0 | 0 |
| 11 | NA | NA | NA | 0 | 3 | 1 |
| 13 | NA | NA | NA | 0 | 5 | 4 |

[1] "% Efficiency" is percentage of efficiency of the test compounds in this assay relative to all-trans-retinoic acid.
[2] "NA" stands for NOT ACTIVE (>10,000)

TABLE 2

Ligand Binding Assay

| | Kd (nanomolar) | | |
|---|---|---|---|
| Compound No. | $RAR_\alpha$ | $RAB_\beta$ | $RAR_\gamma$ |
| 3 | 90 | 44 | 102 |
| 4 | 17 | 14.5 | 59 |
| 6 | 1048 | 113 | 317 |
| 10 | 15 | 14 | 66 |
| 11 | 24 | 34 | 112 |
| 13 | 11 | 4569 | 5694 |
| 15 | 12.5 | 0.8 | 33 |
| 17 | 20 | 24 | 18 |

TABLE 2-continued

Ligand Binding Assay

| | Kd (nanomolar) | | |
|---|---|---|---|
| Compound No. | $RAR_\alpha$ | $RAB_\beta$ | $RAR_\gamma$ |
| 20 | 22.5 | 16 | 84 |
| 22 | 17 | 36 | 162 |
| 25 | 12 | 9 | 22.5 |
| 26 | 11 | 10 | 17 |
| 30 | 48 | 13 | 41 |

Inverse agonists are ligands that are capable of inhibiting the basal receptor activity of unliganded receptors. Recently, retinoic acid receptors, (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 1996, 271, 22692–22696 which is expressly incorporated herein by reference.

In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. EMBO J. 1993, 12, 2349–2360 expressly incorporated herein by reference. Retinoid inverse agonists are able to inhibit the basal luciferase activity in these cells in a dose dependent manner and $IC_{50}s$ measured.

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection.

In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medications for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

General Embodiments and Synthetic Methodology

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

S The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alky. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

Generally speaking, compounds of the invention where Z is an ethyne function are obtained in a sequence of reactions which initially involve the synthesis of a halogenated, preferably brominated, aryl or heteroaryl (in the preferred embodiment phenyl) derivative where the aryl or heteroaryl (preferably phenyl) group corresponds to the Y$_1$ group of Formula 1. This bromo derivative is already substituted with the appropriate Y$_3$(R$_4$)—X— and R$_1$ and R$_2$ groups, or appropriate precursors, or protected precursors thereof The bromo compound is reacted with (trimethylsilyl)acetylene to provide a (2-trimethylsilyl)ethynyl-aryl or (2-trimethylsilyl) ethynyl-heteroaryl derivative, from which the trimethylsilyl group is removed by treatment with base. The ethyne compounds are coupled with a reagent of the formula X$_2$—Y$_2$(R$_2$)-A-B where X$_2$ is a halogen and the remaining symbols are defined in connection with Formula 1.

Compounds of the invention where Z is other than the above-described ethyne function, are obtained by utilizing the reactive nature of the bromo group, either to couple the bromo compound directly, such as in a Heck reaction, to provide compounds where the Y$_2$(R$_2$)A-B group is attached directly to the aryl or heteroaryl (Y$_1$) group. Alternatively the bromo function may be converted into other reactive groups, such as NH$_2$, SH, or COOH which is then coupled to a reagent that together with the NH$_2$, SH, or COOH completes the moiety designated Z in Formula 1, and which also introduces the Y$_2$(R$_2$)-A-B moiety of the compounds of the invention. Compounds of the invention where Z represents an ester, amide, thioester, thioamide, or azo linkage can, for example, be prepared in accordance with this general synthetic methodology. During the synthetic manipulation OH or SH functions or other reactive functions on the Y$_1$, Y$_2$, and Y$_3$ rings may be protected by appropriate acid or base labile protecting groups, such as methoxymethyl (MOM), acetyl or trialkylsilyl. Still further, the Z-Y$_2$(R$_2$)-A-B moiety can be formed in multiple steps starting with the introduction of a two-carbon moiety (such as the CH$_3$CO group) in place of the reactive bromo group of the substituted Y$_1$ nucleus. This type of reaction sequence is suitable, for example, for the preparation of compounds of the invention where Z is —(CR$_3$=CR$_3$)$_n$—, n is 3, 4 or 5 and Y$_2$ represents a direct valence bond between the (CR$_3$=CR$_3$)$_n$. group and B. Details of the above-outlined generalized synthetic schemes are provided below in connection with the description of the specific embodiments and specific examples.

The synthetic methodology employed for the synthesis of the compounds of the present invention may also include transformations of the group designated -A-B in Formula 1. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of q in the compounds of the invention (or precursors thereof) before affecting the coupling or linkage with the phenyl nucleus (where such compounds are not available from a commercial source) aromatic or heteroaromatic carboxylic acids are subjected to homologation by successive treatment under Arndt-Eistert S conditions or other homologation procedures. Alternatively, derivatives which are not carboxlic acids may also be homologated by appropriate procedures. The homologated acids can then be esterified by the general procedure outlined in the preceding paragraph.

Compounds of the invention as set forth in Formula 1 (or precursors thereof) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of the invention or precursors thereof, where the A group has a triple (acetylenic) bond, can be made by reaction of a corresponding aromatic methyl ketone with strong base, such as lithium diisopropylamide, reaction with diethyl chlorophosphate and subsequent addition of lithium diisopropylamide.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 14 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, et al., Tet. Lett., 1979, 399) or dimethyl sulfoxide/oxalyl chloride in methylene chloride (Omura, et al., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of the invention, or precursors thereof, where B is H can be prepared from the corresponding halogenated aromatic or heteroaromatic compounds, preferably where the halogen is I.

Specific Embodiments

With reference to the symbol $Y_1$ in Formula 1, the preferred compounds of the invention are those where $Y_1$ is phenyl, pyridyl, thienyl, furyl and thiazolyl. Among these the phenyl group and pyridyl group are preferred. The $Y_1$ phenyl group is preferably substituted in the 1,2,5 pattern such that the $Y_3(R_4)$—X— group is in the 1 position, the $R_1$ group is in the 2 position and the Z group is in the 5 position. When $Y_1$ is pyridyl it is preferably substituted in the same geometrical pattern, such that the $Y_3(R_4)$—X— and $R_1$ groups are preferably attached to adjacent ring carbons, and preferably one ring atom (carbon or nitrogen) is located between the ring carbons to which the $Y_3(R_4)$—X— and Z groups are respectively attached.

The X group is preferably —O— as in an aryl or heteroaryl ether linkage, and the $R_1$ group is preferably a bulky group, such as a branched chain alkyl, 1-adamantyl, 1-adamantyloxy, 2-tetrahydropyranoxy or trialkylsylanyloxy. The $Y_1$ aryl or heteroaryl group is preferably not substituted with an $R_2$ group, or when it is so substituted $R_2$ is lower alkyl, preferably methyl or F.

Referring now to the linker moiety Z, defined in Formula 1, Z is preferably —C≡C—, —CH=CH—, —CONH—, —COO—, —OCO—, —NHCO—, —CO—$CR_3$=$CR_3$—($CR_3$=$CR_3$)$_n$— and n is 3, or the Z group is absent (n is zero and $Y_2$ is directly attached to the $Y_1$ ring). Among the foregoing, even more preferred are the following: —C≡C—, —C=C—, —CONH—, —COO—, and ($CR_3$=$CR_3$)$_n$ where n is zero.

The $Y_2$ group of Formula 1 is preferably phenyl, naphthyl, pyridyl, thienyl or furyl. Even more preferred are compounds where $Y_2$ is phenyl, naphthyl or pyridyl. As far as substititutions on the $Y_2$ (phenyl), $Y_2$ (pyridyl) and ($Y_2$) naphthyl groups are concerned, compounds are preferred where the phenyl group is 1,4 (para) substituted, the naphthyl group is 2,6 substituted and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no or only one optional $R_2$ substituent on the $Y_2$ group, and the preferred $R_2$ substituent is fluoro (F). The optional $R_2$ substituent is preferably in the position adjacent to the A-B group and between the Z and A-B groups so that, for example, when $Y_2$ is phenyl, and Z is ethynyl and A-B represent a carboxylic acid moiety, then the $Y_2$ phenyl group is substituted in 1 position by COOH, in the 2 position by the $R_2$ group, and in the 4 position by the ethynyl group.

The A-B group of the preferred compounds is ($CH_2$)$_q$COOH or ($CH_2$)$_q$—COOR$_8$, where R$_8$ is defined as above. Even more preferably q is zero and R$_8$ is lower alkyl.

Referring now to the aryl or heteroaryl moiety $Y_3$, the preferred compounds of the invention are those where $Y_3$ is phenyl, pyridyl, thienyl, furyl and thiazolyl. Among these the phenyl group and particularly substituted phenyl are more preferred. Preferably the $Y_3$ group has only one or two $R_4$ substituents, and when $Y_3$ is phenyl $R_4$ is located in the 4 (para) or and 2 (ortho) positions relative to the X group. The $R_4$ substituent is preferably selected from $CF_3$, $NO_2$, $NH_2$, $COOCH_3$, $CH_3$, $N_3$, I, ethyl, or the $R_4$ group is altogether missing.

The most preferred compounds in accordance with Formula 1 are listed below in Table 3 for Formula 2 and with reference to that formula.

TABLE 3

Formula 2

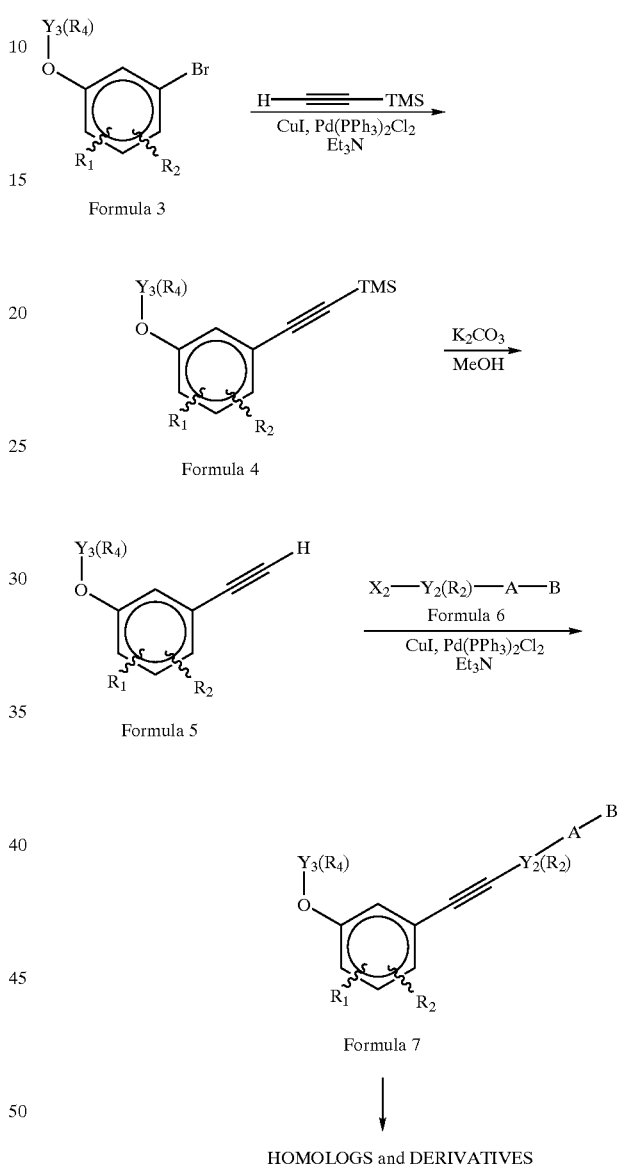

| Compound No. | $R_4$ | $R_4$* | Z | $X_3$ | $R_2$ | $R_8$ |
|---|---|---|---|---|---|---|
| 1 | $CF_3$ | H | —C≡C— | CH | H | Et |
| 2 | $CF_3$ | H | —C≡C— | CH | F | Et |
| 3 | $CF_3$ | H | —C≡C— | CH | H | H |
| 4 | $CF_3$ | H | —C≡C— | CH | F | H |
| 5 | $CF_3$ | H | —C≡C— | N | H | Et |
| 6 | $CF_3$ | H | —C≡C— | N | H | H |
| 7 | $NO_2$ | H | —C≡C— | CH | F | Et |
| 8 | $NH_2$ | H | —C≡C— | CH | F | Et |
| 9 | $COOCH_3$ | H | —C≡C— | CH | F | $CH_2CH_2$—$Si(CH_3)_3$ |
| 10 | $COOCH_3$ | H | —C≡C— | CH | F | H |
| 11 | $NO_2$ | H | —C≡C— | CH | F | H |
| 12 | $CF_3$ | H | —CONH— | CH | F | Et |
| 13 | $CF_3$ | H | —CONH— | CH | F | H |
| 14 | $CH_3$ | H | —CH=CH— | CH | H | Et |
| 15 | $CH_3$ | H | —CH=CH— | CH | H | H |
| 16 | $N_3$ | H | —C≡C— | CH | F | Et |
| 17 | $N_3$ | H | —C≡C— | CH | F | H |
| 18 | I | H | —C≡C— | CH | F | Et |
| 19 | H | H | —C≡C— | CH | F | Et |
| 20 | I | H | —C≡C— | CH | F | H |
| 21 | $CF_3$ | H | —CH=CH— | CH | H | Et |
| 22 | $CF_3$ | H | —CH=CH— | CH | H | H |
| 23 | $CH_3$ | H | —C≡C— | CH | F | Et |
| 24 | $CH_2CH_3$ | H | —C≡C— | CH | F | Et |
| 25 | $CH_2$-$CH_3$ | H | —C≡C— | CH | F | H |
| 26 | $CH_3$ | H | —C≡C— | CH | F | H |
| 27 | $CH_3$ | $NO_2$ | —C≡C— | CH | H | Et |
| 28 | $CH_3$ | $NH_2$ | —C≡C— | CH | H | Et |
| 29 | $CH_3$ | H | —C≡C— | CH | H | Et |
| 30 | $CH_3$ | H | —C≡C— | CH | H | H |
| 31 | $CH_3$ | $NO_2$ | —C≡C— | CH | H | H |
| 32 | $CH_3$ | $NH_2$ | —C≡C— | CH | H | H |
| 33 | $CH_3$ | H | —COO— | CH | H | —$CH_2$—$C_6H_3$ |
| 34 | $CH_3$ | H | —COO— | CH | H | H |
| 35 | $CH_3$ | H | —CONH— | CH | F | Et |
| 36 | $CH_3$ | H | —CONH— | CH | F | H |

The compounds of this invention can be made by the general procedures outlined above under the title ""GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all of the compounds represented by Formula 1.

Reaction Scheme 1

Referring now to Reaction Scheme 1 a synthetic process is disclosed whereby exemplary compounds of the invention are obtained in which, with reference to Formula 1, the Z group is ethynyl (—C≡C—), X is O, the $Y_1$ group is phenyl, substituted in 1,3 (meta) positions by the ethynyl and $OY_3(R_4)$ groups, and the remaining symbols are defined as in connection with Formula 1 The starting material shown in Formula 3 of this reaction scheme is a phenol ether brominated in the meta position that is already substituted with the $R_1$ and optional $R_2$ substituents. The compounds of Formula 3 can be obtained in accordance with the chemical literature or by such modifications of known literature processes which are within the skill of the practicing organic chemist. In addition the experimental section of this application, titled "Specific Examples" discloses the processes for synthesizing specific compounds of Formula 3 which are used in the synthesis of certain exemplary compounds of the invention, and where such starting compounds are not available by known literature processes, nor commercially.

A person skilled in the art will readily understand that although the examplary processes of syntheses described in Reaction Scheme 1 and in the other reaction schemes of this specification depict a phenol ether in Formula 3, analogous procedures can also be performed on compounds where X is S (thioethers), X is $C(R_2)_2$ (diaryl methanes) or X is $NR_3$ (diarylamines). A person skilled in the art will also understand that depending on their nature the $R_1$ and $R_2$ groups may require protection by a suitable blocking group that is removed only at the appropriate, sometimes in the last, step or steps of the synthetic route. Blocking groups for hydroxy, amino, thiol, carboxylic acid and other functions which may be represented by the $R_1$ and $R_2$ groups, their placement on these functions and removal are well known and understood by those skilled in the art. Still further, a peson skilled in the art will be able to adapt the processes disclosed in Reaction Scheme 1 and in the other reaction schemes of this specification to compounds where the starting material corresponding to Formula 3 is not a benzene but rather a heteroaryl derivative ($Y_1$ of Formula 1 is heteroaryl).

Referring now back again specifically to Reaction Scheme 1, examples for the compounds of Formula 3 used for the preparation of the presently most preferred compounds of the invention are: 5-bromo-2-tert-butyl-1-[(4'-methyl)phenoxy]benzene, 5-bromo-2-tert-butyl-1-[(2'-amino-4'-methyl)phenoxy]benzene, and 5-bromo-2-tert-butyl-1-[(4'-ethyl)phenoxy]benzene. Other examples are: 5-bromo-2-(1-adamantyl)-1-[(4'-methyl)phenoxy]benzene, 5-bromo-2-(1-adamantyl)-1-[(2'-amino-4'-methyl)phenoxy] benzene, 5-bromo-2-(1-adamantyl)-1-[(4'-ethyl)phenoxy] benzene, 5-bromo-2-(2-tetrahydropyranyloxy)-1-[(4'-methyl)phenoxy]benzene, 5-bromo-2-(2-tetrahydropyranyloxy) 1-[(2'-amino-4'-methyl)phenoxy] benzene, 5-bromo-2-(2-tetrahydropyranyloxy)-1-[(4'-ethyl) phenoxy]benzene, 5-bromo-2-methoxymethyloxy-1-[(4'-methyl)phenoxy]benzene, 5-bromo-2-methoxymethyloxy-butyl-1-[(2'-amino-4'-methyl)phenoxy]benzene, and 5-bromo-2-methoxymethyloxy-1-[(4'-ethyl)phenoxy] benzene.

As is shown in Reaction Scheme 1, compounds of Formula 3 are reacted with (trimethylsilyl)acetylene in the presence of copper(I)iodide, diethylamine and bis (triphenylphosphine)palladium(II) chloride to yield the diaryl ether derivatives substituted in the meta position relative to the ether function, with the (trimethylsilyl)ethynyl group (Formula 4). The trimethylsilyl group is removed from the compounds of Formula 4 by treatment with base, such as potassium carbonate, in alcoholic solvent (eg. methanol), to yield the ethynyl substituted diaryl ether derivatives of Formula 5. The ethynyl substituted diaryl ether derivatives of Formula 5 are then coupled with the reagent of the formula $X_2$—$Y_2(R_2)$-A-B (Formula 6), where $X_2$ is halogen and the remaining symbols are defined in connection with Formula 1. The coupling reaction is conducted in the presence of copper(I)iodide, diethylamine and bis (triphenylphosphine)palladium(II) chloride to provide the disubstituted acetylene compounds of Formula 7. Examples for the reagent $X_2$—$Y_2(R_4)$-A-B (Formula 6) are ethyl 4-iodobenzoate, ethyl 2-fluoro-4-iodobenzoate, trimethylsilanylethyl 2-fluoro-4-iodobenzoate, ethyl 6-bromo-2-naphthoate, ethyl 6-iodonicotinate, ethyl 2-iodofuran-5-carboxylate, and ethyl 2-iodothiophen-5-carboxylate. Examples for the conditions of the reactions leading from compounds of Formula 5 to the compounds of Formula 7 are described in connection with the specific examples. These reactions are analogous to the reaction described in several United States Letters Patent, such as U.S. Pat. Nos. 5,348, 972 and 5,346,915, assigned to the assignee of the present application, where introduction of an ethynyl group into a heteroaryl nucleus and subsequent coupling with a halogenated aryl or heteroaryl function are described. The specifications of U.S. Pat. Nos. 5,348,972 and 5,346,915 are specifically incorporated herein by reference. The compounds of Formula 7 are within the scope of the invention (Z=—C—C) and can be converted into further homologs and derivatives in reactions of the type generally described above. A frequently used reaction in this regard is saponification whereby an ester function (represented in Formula 7 by the symbol B) is converted into a carboxylic acid function.

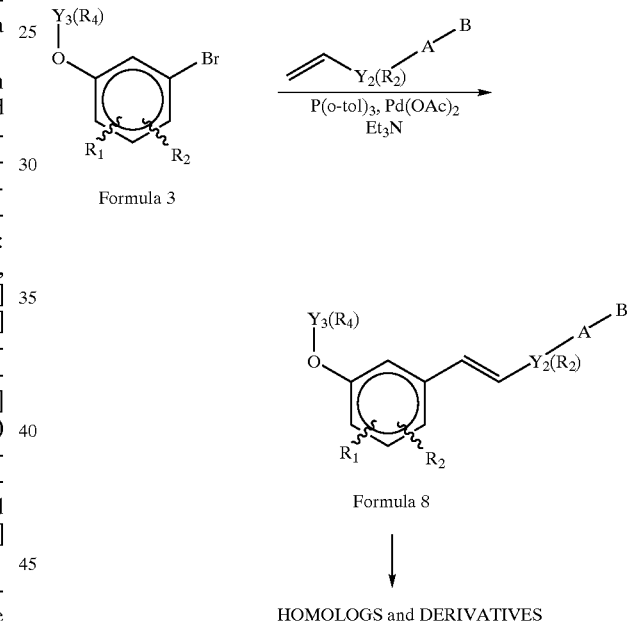

Reaction Scheme 2

Formula 3

Formula 8

HOMOLOGS and DERIVATIVES

Reaction Scheme 2 discloses synthetic processes for obtaining certain exemplary compounds of the invention in which, with reference to Formula 1, the Z group is —CH=CH—. In accordance with this process, brominated diaryl ether derivatives of Formula 3 are reacted in a Heck reaction with vinylaryl compounds of the formula $CH_2$=CH—$Y_2(R_2)$-A-B. Examples for suitable vinylaryl compounds are ethyl 4-vinylbenzoate, ethyl 6-vinyl nicotinate, ethyl 5-vinylfuran-2-carboxylate and ethyl 5-vinylthiophen-2-carboxylate. The Heck reaction is typically conducted in the presence of triethylamine, palladium (II)acetate and tri-(o-tolyl)phosphine. The Heck reaction provides compounds of Formula 8 which are within the scope of the present invention. The compounds of Formula 8 can be converted to further homologs and derivatives still within the scope of the present invention, as described above.

Reaction Scheme 3

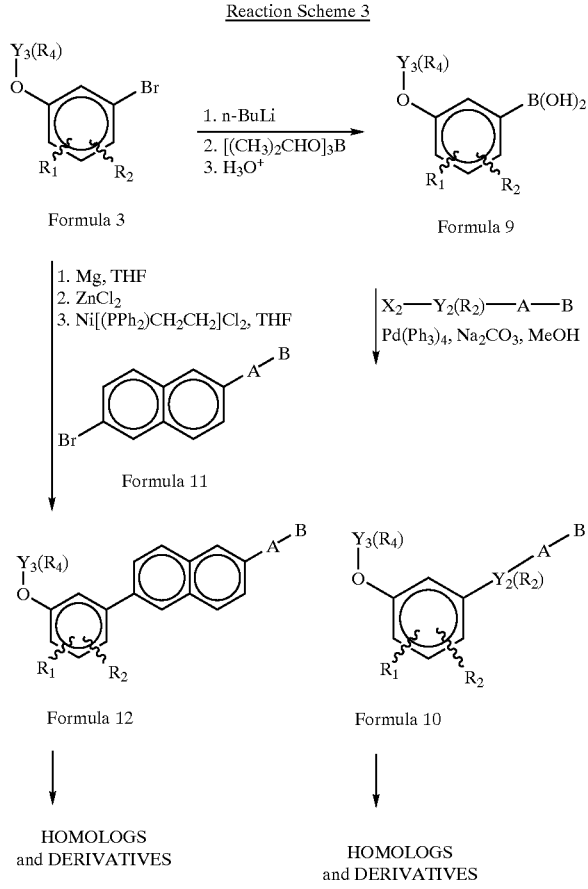

Reaction Scheme 4

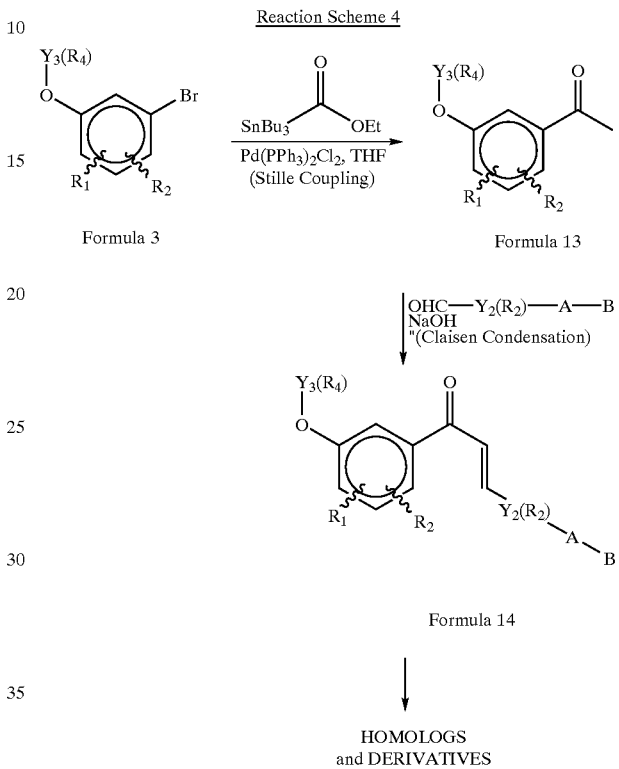

Reaction Scheme 3 discloses a synthetic process for preparing compounds of the invention where, with reference to Formula 1, the Z group is —(CR$_3$═CR$_3$)$_n$— and n is 0. In other words, this is a reaction scheme for obtaining compounds of the invention where the —Y$_2$(R$_2$-A-B moiety is directly linked to the Y$_1$ aromatic ring. In the examples shown in the scheme the —Y$_2$(R$_2$)-A-B moiety is directly linked to the position of the phenyl ring which is meta to the Y$_3$(R$_4$)O— ether moiety. Pursuant to this reaction scheme, the brominated diaryl ether compounds of Formula 3 are reacted with n-butyl lithium and subsequently with triisopropylborate to provide the boronic acid derivative intermediates of Formula 9. The boronic acid derivatives of Formula 9 react with compounds of the formula X$_2$—Y$_2$(R$_2$)-A-B (Formula 6 and X$_2$ is preferably bromine) in the presence of tetrakis[triphenylphosphine]palladium [Pd(PPh$_3$)$_4$] and a base, such as sodium carbonate, to yield compounds of Formula 10. Examples of preferred reagents of formula X$_2$—Y$_2$(R$_2$)-A-B are ethyl 6-bromo-2-naphthoate, ethyl 4-iodobenzoate, ethyl 6-iodonicotinate, ethyl 2-iodofuran-5-carboxylate, and ethyl 2-iodothiophen-5-carboxylate. The compounds of Formula 10 can be converted into further compounds of the invention by the reactions described above, such as saponification, amide formation, homologation and the like.

Reaction Scheme 3 also discloses an alternative route to compounds of the invention where the —Y(R$_2$)-A-B moiety is directly linked to the Y$_1$ aromatic ring, shown for the specific example where the Y$_2$ ring is naphthyl. Thus, the diaryl ether compound of Formula 3 is converted to a Grignard reagent with magnesium in an ether-like solvent, such as tetrahydrofuran. Zinc chloride, ethyl bis (triphenylphosphine)nickel(II) chloride and a halogenated naphthyl derivative of Formula 11 are added to provide the naphthyl diarylether derivatives of Formula 12. An example for the reagent of Formula 11 is ethyl 6-bromo-2-naphthoate. The naphthyl diarylether derivatives of Formula 12 are within the scope of the invention, and can be converted to further homologs and derivatives.

Reaction Scheme 4 discloses a synthetic route for the preparation of exemplary compounds where, with reference to Formula 1, Z is —CO—CR$_3$═CR$_3$—, that is the preparation of compounds which are α-β unsaturated ketone derivatives (chalcones). In accordance with this scheme, the brominated diaryl ether compounds of Formula 3 are reacted with (1-ethoxyvinyl)tributyltin in the presence of bis (triphenylphosphine)palladium(II) chloride to introduce the acetyl group into the position of the phenyl ring which is meta to the Y$_3$(R$_4$)—O-moiety, and yield the acetophenone derivatives of Formula 13. The latter reaction is known in the art as a Stille coupling. The acetophenone derivatives of Formula 13 are then reacted in a condensation reaction with a reagent of the formula OHC—Y$_2$(R$_2$)-A-B to yield compounds of Formula 14 which are within the scope of the invention. An examples for the reagent OHC—Y$_2$(R$_2$)-A-B is 4-carboxybenzaldehyde that is available commercially. Examples of other reagents suitable for the condensation reaction and for the synthesis of compounds of Formula 14 are: 5-carboxy-pyridine-2-aldehyde, 4-carboxy-pyridine-2-aldehyde, 4-carboxy-thiophene-2-aldehyde, 5-carboxy-thiophene-2-aldehyde, 4-carboxy-furan-2-aldehyde, 5-carboxy-furan-2-aldehyde, 4-carboxyacetophenone, 2-acetyl-pyridine-5-carboxylic acid, 2-acetyl-pyridine-4-carboxylic acid, 2-acetyl-thiophene-4-carboxylic acid, 2-acetyl-thiophene-5-carboxylic acid, 2-acetyl-furan-4-carboxylic acid, and 2-acetyl-furan-5-carboxylic acid. The latter compounds are available in accordance with the chemical literature; see for example Decroix et al. J. Chem Res. (S) 1978, 4, 134; Dawson et al. J. Med. Chem. 1983, 29, 1282; and Queguiner et al. Bull. Spc. Chimique de France 1969, 10, 3678–3683. The condensation reaction between the compounds of Formula 13 and the aldehyde of the formula OHC—$Y_2(R_2)$-A-B (or an analogous ketone compound) is conducted in the presence of base in an alcoholic solvent. Preferably, the reaction is conducted in ethanol in the presence of sodium hydroxide. Those skilled in the art will recognize this condensation reaction as an aldol condensation, and in case of the herein described preferred examples (condensing a ketone of Formula 13 with an aldehyde) as a Claisen-Schmidt reaction. (See March: Advanced Organic Chemistry: Reactions, Mechanisms, and Structure, pp 694 695 McGraw Hill (1968). The compounds of Formula 14 are within the scope of the present invention, and can also be subjected to further transformations resulting in additional compounds of the invention designated in the scheme as "homologs and derivatives".

Reaction Scheme 5

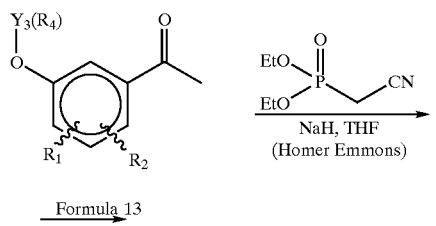

Formula 13

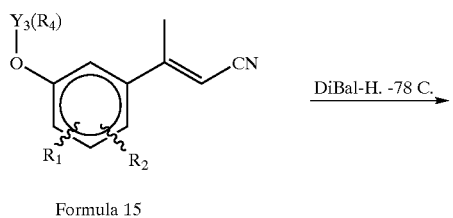

Formula 15

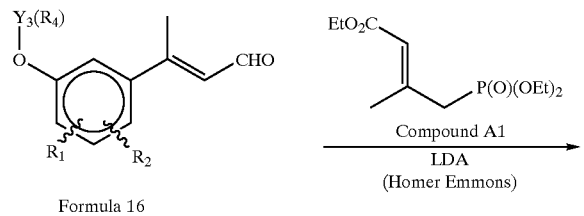

Formula 16

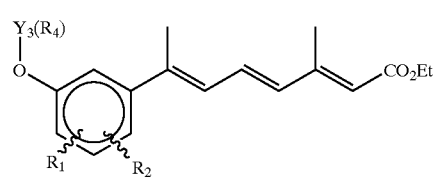

Formula 17

↓

HOMOLOGS and DERIVATIVES

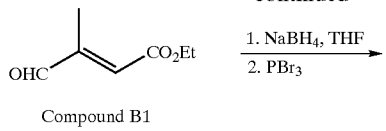

Compound B1

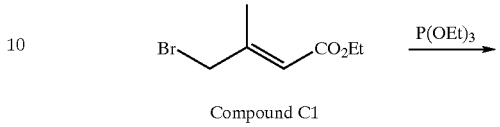

Compound C1

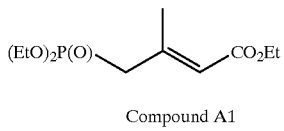

Compound A1

Reaction Scheme 5 discloses a synthetic route for the preparation of compounds where, with reference to Formula 1, Z is —$(CR_3=CR_3)_n$—, n is 3 and the B group is directly attached to the Z group. Thus, in accordance with this scheme the acetophenone derivatives of Formula 13, which can be obtained in accordance with Reaction Scheme 4 in a Stille coupling reaction, are reacted in a Horner Emmons reaction, in the presence of strong base such as lithium diisopropylamide (LDA), with diethylcyanomethyl phosphonate. The latter reagent is commercially available. The product of the Horner Emmons reaction is a biaryl ether compound of Formula 15 that is substituted in the meta position with a 1-methyl-2-cyanoethenyl group. Those skilled in the art will readily understand that instead of a Horner Emmons reaction the compounds of Formula 15 can also be obtained as a result of an analogous Wittig reaction.

Referring still to Reaction Scheme 5, the cyano function of the compounds of Formula 15 is reduced with a mild reducing agent, such as diisobutylaluminum hydride (Dibal-H) to provide the aldehyde compounds of Formula 16. Another Horner Emmons reaction performed on the aldehydes of Formula 16 with the reagent diethyl(E)-3-ethoxycarbonyl-2-methylallylphosphonate (Compound Al) provides compounds of Formula 17 which are within the scope of the present invention. It will be readily apparent to those skilled in the art that the herein described exemplary synthetic process can be readily adapted or modified by utilizing analogous phosphonate or phosponium salt reagents in Horner Emmons or Wittig reactions, respectively, to obtain additional compounds within the scope of Formula 1 in which Z is —$(CR_3=CR_3)_n$—, and n is 3–5. The compounds of Formula 17 can be converted into further compounds within the scope of the invention by reactions such as saponification, amide formation, reduction to the aldehyde or alcohol stage, and the like. This is indicated in the reaction scheme by conversion to "homologs and derivatives".

Reaction Scheme 5 also discloses the process of preparing the reagent of Compound A1, starting from the commercially available ethyl (Z)-3-formyl-2-butenoate (Compound B1). In this preparation the aldehyde function of Compound B1 is reduced with sodium borohydride, and the resulting primary alcohol is reacted with phosphorous tribromide. The resulting ethyl (Z)-3-bromo-2-butenoate (Compound C1) is reacted with triethyl phosphonate to give Compound A1 (See Corey et al. J. Org. Chem. 1974, 821).

Reaction Scheme 6

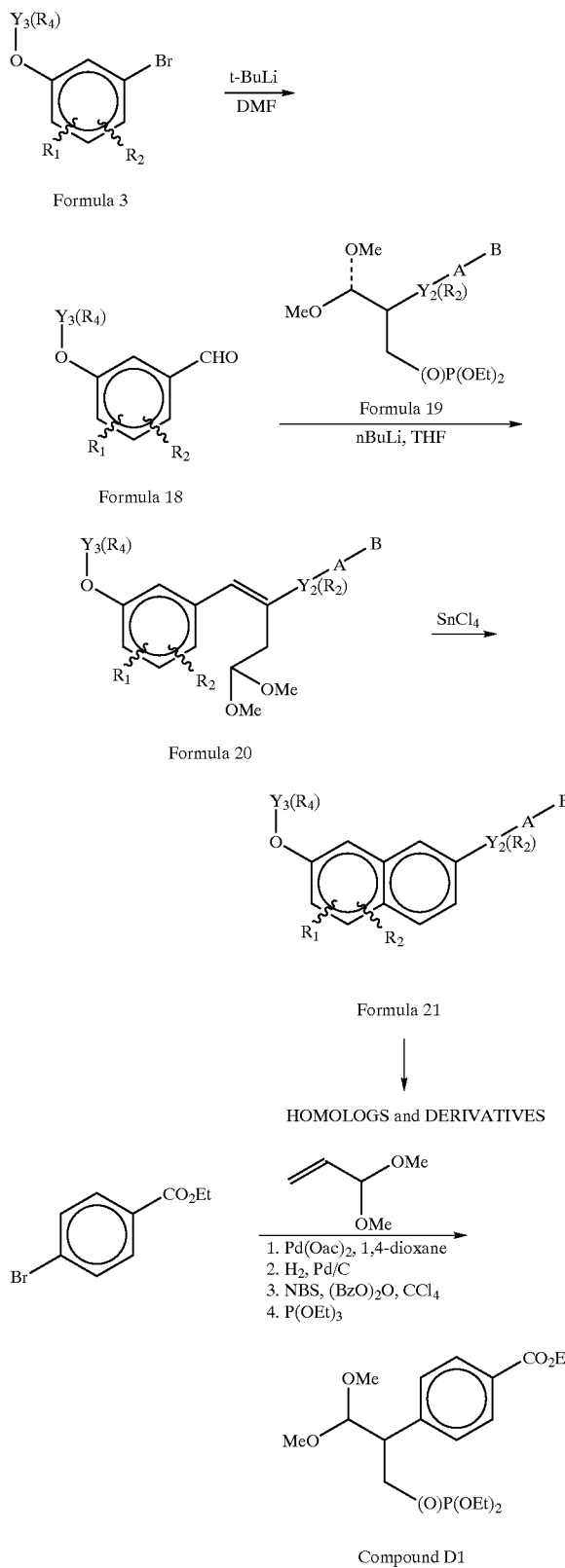

Reaction Scheme 6 provides an example for synthesis of compounds of the invention where the $Y_1$ group is naphthyl substituted in the 2 and 7 positions by the $Y_3(R_4)O$ and Z groups, and where Z is —$(CR_3=CR_3)_n$—, n is 0. More specifically, Reaction Scheme 6 provides an example for synthesis of compounds of the invention where the $Y_1$ naphthyl group is directly attached to the $Y_2$-A-B group. In accordance with this reaction scheme, the brominated diaryl ether derivatives of Formula 3 are reacted with dimethylformamide in the presence of t-butyl lithium to yield the benzaldehyde derivatives of Formula 18. The benzaledehyde derivatives of Formula 18 are subjected to a Horner Emmons type reaction, in the presence of strong base such as n-butyl lithium in hexane, with a 1-aryl or 1-heteroaryl 1-diethoxyphosphoryl-3,3-dimethoxypropane derivative of Formula 19. An example of the phosphonate compound in accordance with Formula 19 is ethyl 4-(diethoxyphosphoryl-3,3-dimethoxypropyl)benzoate (Compound D1). Ethyl-4-(diethoxyphosphoryl-3,3-dimethoxypropyl)benzoate (Compound D1) is available in accordance with the procedure of EPO Application No. 0 210 929 (published on Feb. 4, 1987, Shroot et al.) which is incorporated herein by reference. In accordance with the Shroot et al. reference the reagent ethyl 4-(diethoxyphosphoryl-3,3-dimethoxypropyl)benzoate is made starting with ethyl 4-bromobenzoate that is reacted with dimetyl acetal of acryl aldehyde, the product is hydrogenated and subsequently brominated (with N-bromo succinimide) and thereafter reacted with triethylphosphite as is shown in the reaction scheme.

Other examples for the phoshonates of Formula 19 are ethyl 2-(diethoxyphosphoryl-3,3-dimethoxypropyl) pyridine-5-carboxylate, ethyl 2-(diethoxyphosphoryl-3,3-dimethoxypropyl)pyridine-6-carboxylate, ethyl 2-(diethoxyphosphoryl-3,3-dimethoxypropyl)thiophene-4-carboxylate, ethyl 2-(diethoxyphosphoryl-3,3-dimethoxypropyl)thiophene-5-carboxylate, ethyl 2-(diethoxyphosphoryl-3,3-dimethoxypropyl)furan-4carboxylate, ethyl 2-(diethoxyphosphoryl-3,3-dimethoxypropyl)furan-5-carboxylate. These and analogous phosphonate reagents within the scope of Formula 19 can be obtained by appropriate modification of the procedure described in the Shroot et al. reference.

The product of the Horner Emmons reaction between the diaryl ether aldehydes of Formula 18 and the 1-aryl or 1-heteroaryl 1-diethoxyphosphoryl-3,3-dimethoxypropane derivative of Formula 19 is a disubstituted ethene compound of Formula 20. Those skilled in the art will readily understand that instead of a Horner Emmons reaction, a Wittig reaction can also be employed, utilizing the appropriate phosphonium derivative, to provide compounds of Formula 20.

The disubstituted ethene compounds of Formula 20 are cyclized, for example by heating in a neutral solvent (such as dichloromethane), in the presence of $SnCl_4$ or other suitable Friedel Crafts type catalyst, to form the "B ring" of the naphthalene derivatives of the invention, as shown in Formula 21. The compounds of Formula 21 can be converted into further compounds of the invention by reaction well known to the synthetic organic chemist, such as saponification, esterification, amide formation and homologation. This is indicated in Reaction Scheme 1 as conversion to "homologs and derivatives".

Reaction Scheme 7

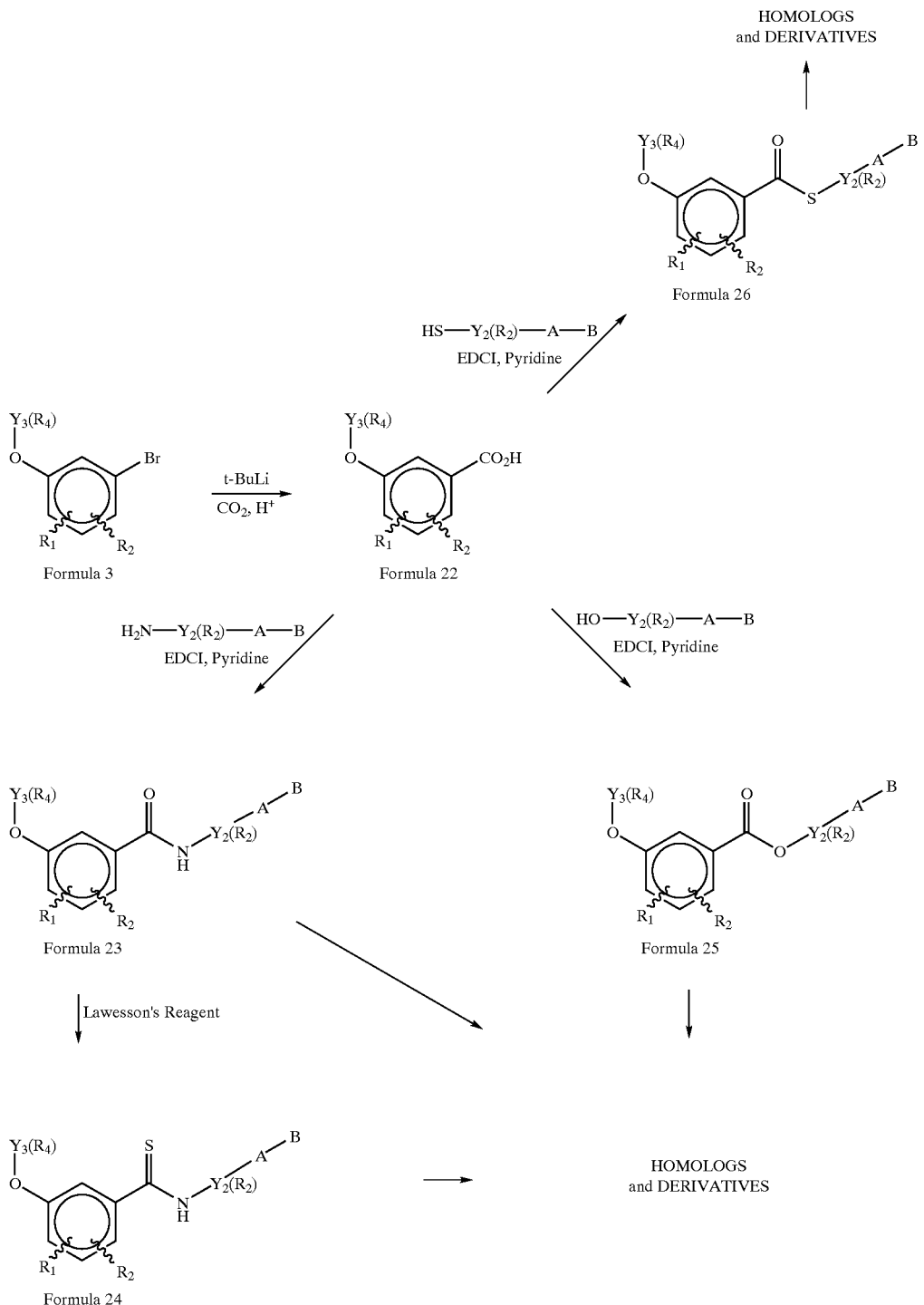

Referring now specifically to Reaction Scheme 7, it discloses synthetic routes to compounds of the invention where, with reference to Formula 1, Z is —CONH— (amides), —COO— (esters) —COS— (thioesters) and —CSNH— (thioamides). In accordance with this scheme the brominated diaryl ether compounds of Formula 3 are reacted with n-butyl lithium and carbon dioxide to "capture" the carbon dioxide and to provide the diaryl ether benzoic acid derivatives of Formula 22. The aryl vinylbenzoic acid derivatives of Formula 22 can be converted into amides of Formula 23 by reaction with reagents of the formula $H_2N$—$Y_2(R_2)$-A-B, into esters of Formula 25 by reaction with reagents of the formula HO—$Y_2(R_2)$-A-B, and into thioesters of Formula 26 by reaction with reagents of the formula HS—Y$_2$(R$_2$)-A-B, where the symbols are defined as in connection with Formula 1. Examples for the reagents of formula H$_2$N—Y$_2$(R$_2$)-A-B are ethyl 4-aminobenzoate and ethyl 6-aminonicotinate, for the reagents of the formula HO—Y$_2$(R$_2$)-A-B ethyl 4-hydroxybenzoate and ethyl 6-hydroxynicotinate, and for the reagents of the formula HS—Y$_2$(R$_2$)-A-B ethyl 4-mercaptobenzoate and ethyl 6-mercaptonicotinate. The reactions between the carboxylic acids of Formula 22 and the reagents of the formulas H$_2$N—Y$_2$(R$_2$)-A-B, HO—Y$_2$(R$_2$)-A-B and HS—Y$_2$(R$_2$)-A-B, can be performed in several ways in which amides, esters and thioesters are normally prepared. For example, the carboxylic acids of Formula 22 can be activated to form an acid chloride or an activated ester which is thereafter reacted with the amines, alcohols or thioalcohols of the above formulas. More advantageously, however, the formation of the amides, esters or thioesters is performed by condensation of the carboxylic acid of Formula 22 with the amines, alcohols or thiols in a suitable aprotic solvent, such as pyridine, in the presence of a condensing agent such as dicyclohexylcarbodiimide (DCC) or more preferably 1-(3-dimethylaminopropyl)-3-ethylcarbodiimidehydrochloride (EDCl). The amide derivatives of Formula 23 can be readily converted to the thioamides of Formula 24 by reaction with [2,4-bis(4methoxyphenyl)-1,3dithia-2,4-diphosphetane-2,4-disulfide] (Lawesson's reagent). The amide derivatives of Formula 23 where the symbol B represents an ester function (such as COOEt) can be readily saponified by treatment with aqueous base, for example LiOH or NaOH, to yield the corresponding amide derivatives where B represents a free carboxylic acid or its salt. Similar saponification of the esters of Formula 25, or of the thioesters of Formula 26, however is problematic because of the lability of the internal ester and thioester functions. The free acids of these derivatives (where B is COOH or a salt thereof) can be obtained by hydrogenation of the corresponding benzyl esters in which B represents COOCH$_2$C$_6$H$_5$. Benzyl 4-hydroxybenzoate a reagent within the scope of HO—Y$_2$(R$_2$)-A-B, can be obtained by reaction of 2-benzyl-1,3-diisopropylurea with 4-hydroxybenzoic acid, as is described in the Specific Examples.

Synthetic routes for the preparation of compounds of Formula 1 where the Z is — —NHCO— (amide), —NHCS— (thioamide), —OCO— (ester) and SCO— (thioester), of the order "reverse" to the one described in connection with Reaction Scheme 7, as well as where Z is —N=N-(azo) and —N=N(=O)— (azoxide) are disclosed in Reaction Schemes 8, 9 and 10. As is shown first in Reaction Scheme 8, the diarylether benzoic acid derivatives of Formula 22 are first converted to the acid chloride, and subsequently to the azide, which are then treated with acid to cause a Curtius rearrangement, followed by hydrolysis to yield the diaryl ether aniline derivatives of Formula 27. These are reacted with the acid chlorides of formula ClCO—Y$_2$(R$_2$)-A-B to yield the amides of Formula 28 which are within the scope of the invention. The amides of Formula 28 are converted into thioamides of Formula 29 by treatment with [2,4-bis(4-methoxyphenyl)-1,3-dithia-2,4-diphosphetane-2,4-disulfide] (Lawesson's reagent). The amides and thioamides of Formula 28 and 29 can be subjected to transformations (including saponification of an ester group when B is COOR$_8$) to yield further compounds within the scope of the present invention.

Reaction Scheme 9

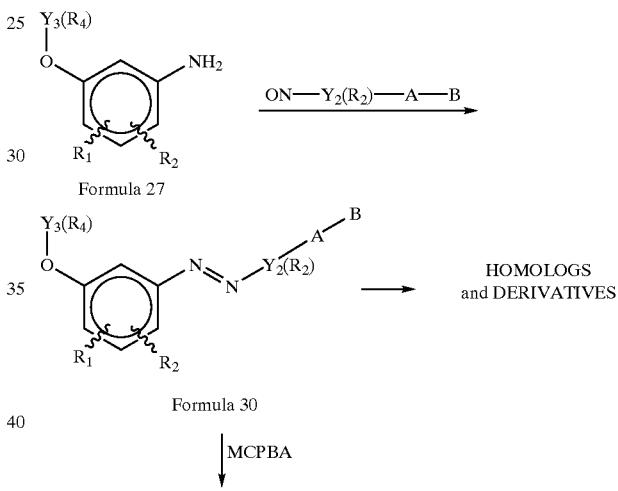

Reaction Scheme 8

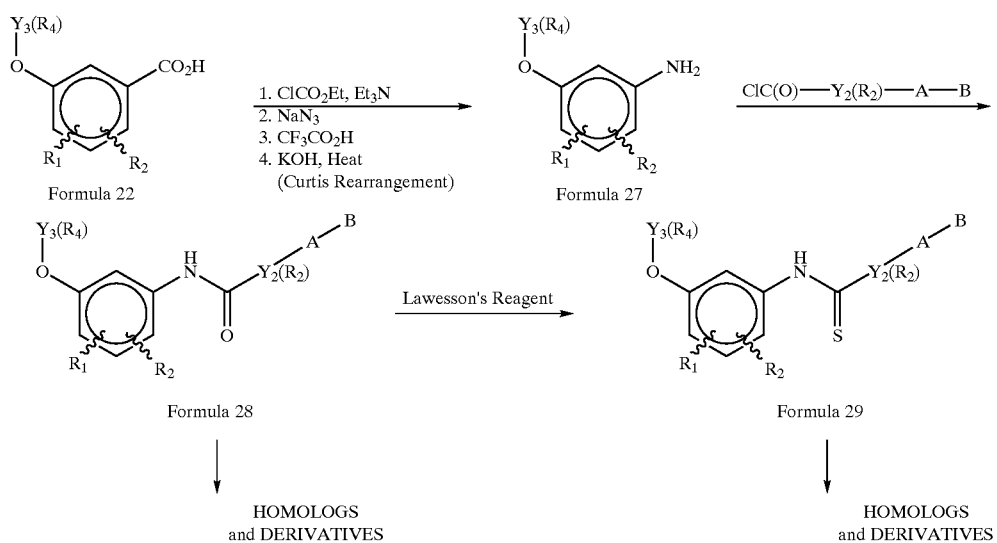

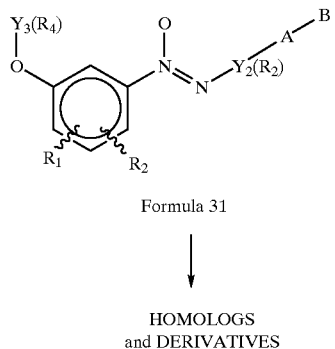

Formula 31

↓

HOMOLOGS
and DERIVATIVES

As is shown in Reaction Scheme 9 the diarylether aniline derivatives of Formula 27 are reacted with nitroso compounds of the formula ON—$Y_2(R)$-A-B, to yield azo compounds of Formula 30. Examples for reagents of formula ON—$Y_2(R_2)$-A-B are ethyl 4-nitrosobenzoate, ethyl 6nitroso-2-naphthoate, ethyl 4-nitrosobenzoate, ethyl 6nitroso-nicotinate, ethyl 2-nitroso-furan-5-carboxylate, and ethyl 2-nitroso-thiophen-5-carboxylate. The azo compounds of Formula 30 can be converted to the azoxy compounds of Formula 31 by oxidation with oxidizing agents known in the art, for example with meta-chloroperoxybenzoic acid (MCPBA).

Referring now to Reaction Scheme 10, the diaryl ether aniline derivatives of Formula 27 are converted to diazonium salt and thereafter to the phenol derivatives of Formula 32. The phenol derivatives of Formula 32 are then converted into esters of Formula 33 by reaction with the acid chlorides of the formula ClCO—$Y_2(R_2)$-A-B or with other activated forms of the carboxylic acids of the general formula HOCO—$Y_2(R_2)$-A-B. As it is described in connection with Reaction Scheme 8, the ester formation may be affected with the free carboxylic acid in an aprotic solvent, such as pyridine, in the presence of dicyclohexylcarbodiimide (DCC) or more preferably 1-(3-dimethylaminopropyl)-3-ethylcarbodiimidehydrochloride (EDCl). In order to obtain free carboxylic acids within the scope of Formula 33 (compounds where B is COOH or a salt thereof) the benzyl ester (B COOCH$_2$C$_6$H$_5$) is prepared first, and the benzyl protecting group is thereafter removed by hydrogenation.

Reaction of the phenol derivatives of Formula 32 with dimethylthiocarbamoyl chloride (($CH_3)_2$NCSCl followed by thermal rearrangement and then by treatment with aqueous base provides the thiophenol derivatives of Formula 34. The thiophenols of Formula 34 are reacted with the acid chlorides of the formula ClCO—$Y_2(R_2)$-A-B, or with other activated forms of the carboxylic acids of the general formula HOCO—$Y_2(R_2)$-A-B to yield the thioesters of Formula 35 within the scope of the present invention. The formation of the thioesters of Formula 35 can be accom- Reaction Scheme 10

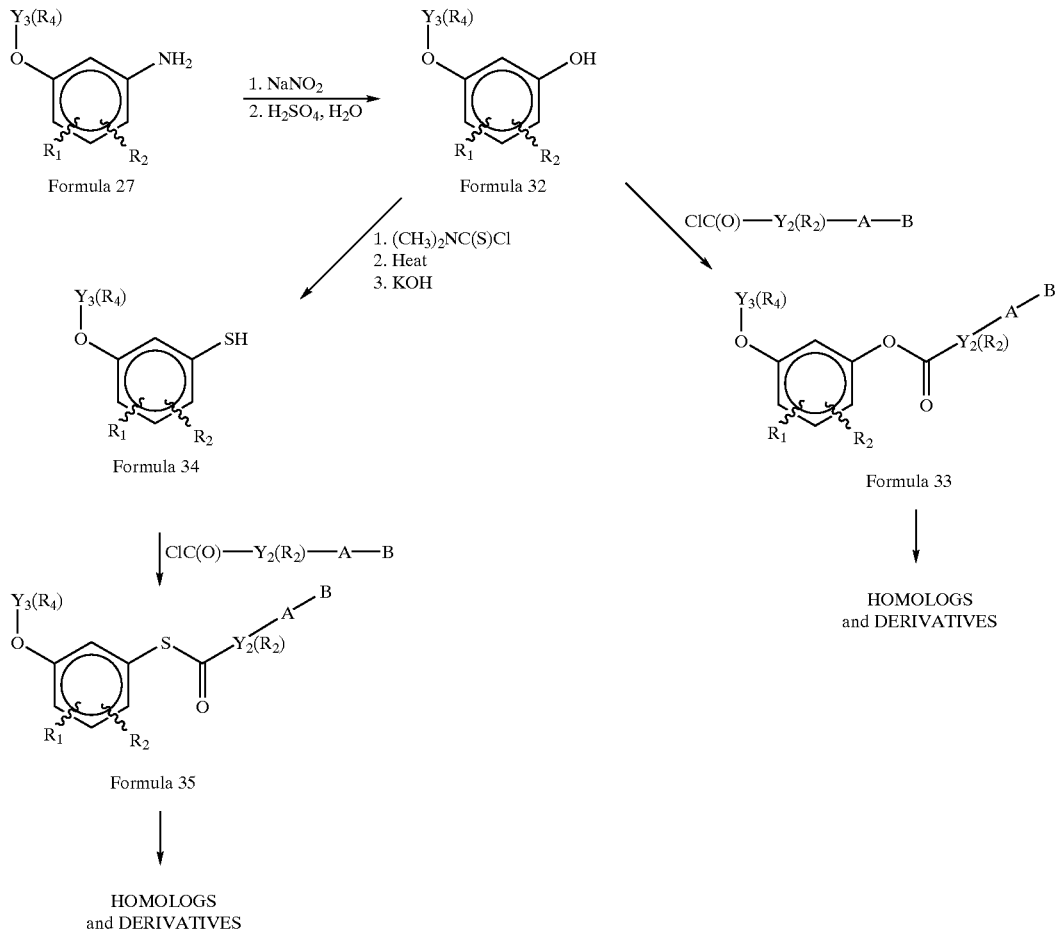

plished under conditions similar to the formation of the esters of Formula 33.

Reaction Scheme 11

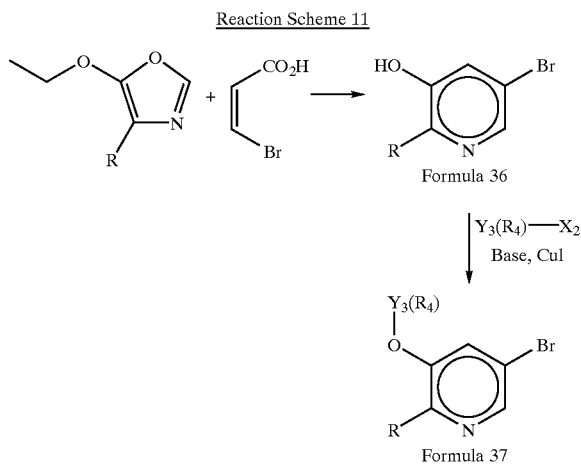

Formula 36

Formula 37

As it was noted above, compounds of the invention where the $Y_1$ group is not phenyl but naphthyl or heteroaryl can be made in analogy to the exemplary synthetic processes disclosed above. In analogy to the reactions schemes shown above, the starting compound is a halogenated, preferably brominated or iodinated heteroaryl derivative that already has a the $Y_3(R_4)O$—, $Y_3(R_4)S$—, $Y_3(R_4)C(R_3)_2$— or $Y_3(R_4)NR_3$—, $R_1$ and the optional $R_2$ substituents. Such compounds, can generally speaking be obtained in accordance with the chemical literature. Reaction Scheme 11, discloses examples for syntheses of bromopyridine derivatives which are analogous to the diaryl ether compounds of Formula 3 and suitable as starting compounds in the above described exemplary synthetic routes. Thus, reaction of an alkyloxazolyl ether (R=alkyl) with bromoacrylic acid, in accordance with the literature procedure of Johnsen, B. et al. Acta Chem. Scand. Ser. B. 1983, 37 907–910, (incorporated herein by reference) yields a 3-bromo-5-hydroxy-6-alkyl pyridine derivative of Formula 36. The bromo derivative of Formula 36 is reacted in the presence of strong base with a reagent of the formula $Y_3(R_4)$—$X_2$ where $X_2$ is a halogen, preferably bromine or fluorine to provide compounds of Formula 37. An example for a reagent of the formula $Y_3(R_4)$—$X_2$ is para tolyl fluoride.

SPECIFIC EXAMPLES

Ethyl 4-iodobenzoate (Compound A)

To a suspension of 24.9 g (100.4 mmol) of 4-iodobenzoic acid in 46.25 g (58.9 mL, 1.0 mol) of ethanol was added 3 mL of c. sulfuric acid. The resulting mixture was refluxed for 60 minutes, distilled until a clear, homogeneous solution was obtained and then allowed to cool to room temperature. The reaction mixture was extracted and partitioned between pentane (250 mL) and water (250 mL) and the layers were separated. The aqueous phase was washed with 3×100 mL-portions of pentane. All organic phases were combined, washed with brine, dried over $MgSO_4$, filtered and concentrated in vacuo to a dark yellow oil. Purification by flash chromatography (silica, 10% ethyl acetate in hexane) yielded the title compound as a clear, light yellow oil. PMR ($CDCl_3$): δ 1.39 (3H, t, J=7.2 Hz), 4.37 (2H, q, J=7.2 Hz), 7.73–7.82 (4H, m).

2-Fluoro-4-iodobenzoic Acid (Compound B)

A round bottom (RB) flask containing a solution of 8.0 g (27.0 8 mmol) of sodium dichromate in 44 mL of glacial acetic acid was placed in an external water bath (21° C.) and left exposed to air. To the resultant orange slurry was added 3.2 g (13.6 mmol) of 2-fluoro-4-iodotoluene followed by the dropwise addition of 22 mL of c. sulfuric acid via syringe (caution: if added too quickly there is a tendency for the mixture to erupt). After the addition of approximately 8 mL of sulfuric acid, a green solid precipitated and the water bath temperature had risen (25° C.). The green reaction mixture was heated in an oil bath (90° C.) for one hour, allowed to cool to ambient temperature, diluted with 1N NaOH solution (aq.) and ethyl acetate (500 mL) and then quenched with sat. $NaHCO_3$ (aq.) solution. The organic phase was separated and washed with water and brine, dried over $MgSO_4$, filtered and concentrated in vacuo to an orange oil. Residual acetic acid was removed by further extraction between ethyl acetate and sat. $NaHCO_3$ (aq.) solution and washing of the organic phase with water and brine. The organic phase was dried over $MgSO_4$, filtered and concentrated in vacuo to give the title compound as an orange solid.

PMR (DMSO-$d_6$): δ 7.61 (1H, t, J=8.0 Hz, J (C—F)=8.0 Hz), 7.67 (1H, dd, J=1.5, 8.2 Hz), 7.78 (1H, dd, J=1.5 Hz, J (C—F)=8.9 Hz).

Ethyl 2-fluoro-4-iodobenzoate (Compound C)

To a solution of 2.5 g (27.0 mmol) of 2-fluoro-4-iodobenzoic acid (Compound B) in 11 mL (8.6 g, 187.5 mmol) of ethanol was added 0.3 mL of c. sulfuric acid. The reaction mixture was heated to reflux in an oil bath (90° C.) for 1.75 hours, fitted with a short path distillation apparatus, distilled and then allowed to cool to ambient temperature. The reaction mixture was extracted and partitioned between pentane and water and the layers were separated. The aqueous phase was washed with pentane and the organic phases were combined. The combined organic phase was washed sequentially with sat. $NaHCO_3$ (aq.) solution, water and brine, dried over $MgSO_4$, filtered and concentrated in vacuo to a purple oil. Purification by flash chromatography (silica, 10% ethyl acetate in hexane) gave the title compound as an orange oil.

PMR ($CDCl_3$): δ 1.39 (3H, t, J=7.1 Hz), 4.39 (2H, q, J=7.1 Hz), 7.52–7.67 (3H, m).

Trimethylsilanylethyl 2-fluoro-4-iodobenzoate (Compound D)

To a solution of 115.5 mg (0.4 mmol) of 2-fluoro-4-iodobenzoic acid (Compound B) in 10 mL of dichloromethane (under a blanket of argon) was added 91.5 mg (0.5 mmol) of 1-(3-dimethylaminopropyl-3-ethyl carbodiimide hydrochloride) and 53 mg (0.4 mmol) of 4-dimethylaminopyridine. To this reaction mixture was added 0.16 ml (132 mg, 1.1 mmol) of 2-trimethylsilylethanol and the resultant mixture was allowed to stir at ambient temperature for 23 hours. The reaction mixture was extracted between ethyl ether and water and the layers were separated. The aqueous phase was washed with ethyl ether (2×50 mL) and the organic phases were combined. The combined organic phase was washed with brine, dried over $MgSO_4$, filtered and concentrated in vacuo to a clear, colorless oil. Purification by flash chromatography (silica, 3% ethyl acetate in hexane) gave the title compound as a clear, colorless oil.

PMR ($CDCl_3$): δ 0.07 (9H, s), 1.13 (2H, dd, J=8.5, 10.3 Hz), 4.42 (2H, q, J=8.5, 10.3 Hz), 7.50–7.70 (3H, m).

Ethyl 2-fluoro-4-aminobenzoate (Compound E)

Commercially available 2-fluoro-4-iodotoluene was converted into the title compound using the literature procedure described by Teng et. al., J. Med. Chem, 1996, 39, 3035–3038, incorporated herein by reference.

PMR ($CDCl_3$): δ 1.37 (3H, t, J=7.1 Hz), 4.14 (2H, br s), 4.33 (2H, q, J=7.1 Hz), 6.33 (1H, dd, J=2.2, J (C—F)=13.0

Hz), 6.41 (1H, dd, J=2.2, 8.6 Hz), 7.77 (1H, d, J=8.4 Hz, J (C—F)=8.4 Hz).

Ethyl 4-vinylbenzoate (Compound F)

Employing the same general procedure as for the preparation of trimethylsilanylethyl 2-fluoro-4-iodobenzoate (Compound D), 323 mg (2.2 mmol) of 4-vinylbenzoic acid was converted into the title compound using 462 mg (2.4 mmol) of 1-(3-dimethylaminopropyl-3-ethyl carbodiimide hydrochloride), 264 mg (2.2 mmol) of 4-dimethylaminopyridine, 0.32 ml (250 mg, 5.45 mmol) of ethanol and 16 mL of dichloromethane. Purification by flash chromatography (silica, 10% ethyl acetate in hexane) gave the title compound as a clear, colorless oil.

PMR (CDCl$_3$): δ 1.39 (3H, t, J=7.2 Hz), 4.37 (2H, q, J=7.2 Hz), 5.38 (1H, d, J=10.8 Hz), 5.86 (1H, d, J=17.6 Hz), 6.75 (1H, dd, J=10.8, 17.6 Hz), 7.46 (2H, d, J=8.4 Hz), 8.00 (2H, d, J=8.4 Hz).

Ethyl 6-iodo-3-nicotinoate (Compound G)

Commercially available 6-chloronicotinic acid was converted into 6-iodo-3-nicotinic acid using the literature procedure described by Newkom et. al., J. Org. Chem., 1986, 51, 953–954, incorporated herein by reference. 6-iodo-3-nicotinic acid was converted into the title compound using the procedure described by Chandraratna et. al., U.S. Pat. No. 5,264,578, incorporated herein by reference.

PMR (CDCl$_3$): δ 1.41 (3H, t, J=7.1 Hz), 4.41 (2H, q, J=7.1 Hz), 7.85 (1H, d, J=8.2 Hz), 7.91 (1H, dd, J=2.1, 8.2 Hz), 8.94 (1H, d, J=2.1 Hz).

5-Bromo-2-tert-butylphenol (Compound H)

To a solution of 29.5 g (170.3 mmol) of 3-bromophenol in 100 mL of carbon tetrachloride (under a blanket of argon) was added 16.4 g (221.3 mmol) of 2-methyl-2-propanol followed by 20 mL of conc. sulfuric acid. The reaction mixture was allowed to stir at ambient temperature for 3.5 days. The clear, colorless solution turned pink and eventually turned purple in color. The reaction mixture was neutralized with sat. NaHCO$_3$ (aq.) solution and then extracted between water and dichloromethane. The layers were separated and the aqueous phase was washed with dichloromethane. The organic phases were combined and washed with brine, dried over MgSO$_4$, filtered and concentrated in vacuo to a purple oil. Purification by flash chromatography (silica, 5% ethyl acetate in hexane) followed by kugelrohr distillation (85–95° C., 2 mm Hg) gave the title compound as a clear, slightly yellow oil.

PMR (CDCl$_3$): δ 1.38 (9H, s), 4.93 (1H, s), 6.84 (1H, d, J=2.1 Hz), 6.99 (1H, dd, J=2.1, 8.2 Hz), 7.12 (1H, d, J=8.2 Hz).

5-Bromo-2-tert-butyl-1-[(2'-amino-4'-methyl)phenoxy] benzene (Compound I)

To a solution of 476 mg (2.1 mmol) of 5-bromo-2-tert-butylphenol (Compound H) in 8 mL of pyridine (under a blanket of argon) was added 457 mg (3.7 mmol) of potassium t-butoxide followed by 752 mg (3.95 mmol) of cuprous iodide a couple minutes later. To this brown mixture was added 546 mg (2.1 mmol) of 4-iodo-3-nitrotoluene. The reaction mixture was heated to reflux (120° C.) for 3 hours and thereafter the mixture was allowed to slowly cool on its own to ambient temperature (with stirring for 26.5 hours). The reaction mixture was extracted between ethyl ether and 10% HCl (aq.) solution and the layers were separated. The aqueous phase was washed with ethyl ether and the organic phases combined, washed with 5N NH$_4$OH (aq.) solution (2×25 mL-portions) and sat. NH$_4$Cl (aq.) solution, dried over Na$_2$SO$_4$, filtered and concentrated in vacuo to a brown oily residue. Purification by flash chromatography (silica, 5% ethyl acetate in hexane) gave crude 2-tert-butyl-5-bromo-1-[(4'-methyl-2'-nitro)phenoxy]benzene. The crude sample was converted into the title compound by dissolving in 5 mL of ethyl acetate and 1 mL of methanol, adding 15 mg of 10% Pd/C and stirring under a hydrogen balloon for 2 days (the hydrogenation reaction is difficult to complete in 100% ethyl acetate as solvent). The reaction mixture was filtered through celite, concentrated in vacuo and purified by flash chromatography (silica, 5% ethyl acetate in hexane) to give the title compound as a yellow oil.

PMR (CDCl$_3$): δ 1.42 (9H, s), 2.37 (3H, s), 5.18 (2H, br s), 6.68 (1H, d, J=8.0 Hz), 6.74 (1H, dd, J=1.6, 8.0 Hz), 6.76 (1H, d, J=1.9 Hz), 7.12 (1H, dd, J=1.9, 8.4 Hz), 7.19 (1H, d, J=1.6 Hz), 7.23 (1H, d, J=8.4 Hz).

5-Bromo-2-tert-butyl-1-[(4'-methyl)phenoxy]benzene (Compound J)

To a cold solution (0° C.) of 27 mg (0.08 mmol) of 5-bromo-2-tert-butyl-1-[(2'-amino-4'-methyl)phenoxy] benzene (Compound I) in 1.2 mL of ethanol (under a blanket of argon) was added 0.5 mL of trifluoroacetic acid followed by 0.5 mL of isoamyl nitrite. The mixture was stirred at 0° C. for 30 minutes and then 0.16 mL of hypophosphorous acid was added. The ice bath was removed and the reaction mixture was allowed to warm on its own to ambient temperature and stirred for 22.5 hours. The reaction mixture was extracted between ethyl acetate and sat. NaHCO$_3$ (aq.) solution and the layers were separated. The organic phase was dried over MgSO$_4$, filtered and concentrated in vacuo to a yellow residue. Purification by flash chromatography (silica, 1% ethyl acetate in hexane) gave the title compound as a clear, colorless oil.

PMR (CDCl$_3$): δ 1.40 (9H, s), 2.35 (3H, s), 6.86–6.92 (3H, m), 7.11 (1H, dd, J=2.0, 8.6 Hz), 7.16 (2H, d, J=8.6 Hz), 7.23 (2H, d, J=8.6 Hz).

2-tert-Butyl-5-trimethylsilanylethynyl-1-[(4'-trifluoromethyl)phenoxy]benzene (Compound K)

To a solution of 423 mg (1.85 mmol) of 5-bromo-2-tert-butylphenol (Compound I) in 2 mL of pyridine (under a blanket of argon) was added 196 mg (1.75 mmol) of potassium t-butoxide. The solution became orangish-brown in color. To this solution was added a solution of 352 mg (1.85 mmol) of cuprous iodide and 0.14 mL (260 mg, 1.0 mmol) of 4-iodobenzotrifluoride in 4 mL of pyridine. The reaction mixture was heated to reflux (120° C.) for 3 hours and thereafter the mixture allowed to slowly cool on its own to ambient temperature (with stirring for 16.25 hours). The reaction mixture was concentrated in vacuo, extracted between ethyl ether and 10% HCl (aq.) solution and the layers separated. The aqueous phase was washed with ethyl ether and the organic phases were combined, washed with 5N NH$_4$OH (aq.) solution (2×25 mL-portions) and sat. NH$_4$Cl (aq.) solution, dried over Na$_2$SO$_4$, filtered and concentrated in vacuo to a brown residue. Purification by flash chromatography (silica, 100% hexane) gave crude 2-tert-butyl-5-bromo-1-[(4'-trifluoromethyl)phenoxy]benzene as a clear, colorless oil. In a sealed tube vessel, a solution of 290 mg (0.8 mmol) of crude 2-tert-butyl-5-bromo-1-[(4'-trifluoromethyl)phenoxy]benzene in 11 mL of triethylamine was sparged (with a stream of argon bubbled vigorously into the solution) for several minutes. To this solution was added 34 mg (0.2 mmol) of cuprous iodide and the resultant mixture was sparged with argon for several minutes. To this reaction mixture was then added 133 mg (0.2 mmol) of bis(triphenylphosphine)palladium(II) chloride. After sparging with argon for several minutes, 0.8 mL (7.8 mmol) of trimethylsilyl acetylene was added to the reaction mixture. The pressure tube was then sealed and heated in an oil bath (75° C.) for 4 days. The reaction mixture was filtered through celite and washed with ethyl ether (100 mL). The filtrate was extracted with water (3×75 mL-portions) and brine, dried over MgSO$_4$, filtered and concentrated in vacuo to give a dark brown oil residue. Purification by flash chromatography (silica, 100% hexane) gave the title compound as a clear, colorless oil.

PMR (CDCl$_3$): δ 0.21 (9H, s), 1.36 (9H, s), 6.94 (1H, d, J=1.7 Hz), 7.02 (2H, d, J=8.5 Hz), 7.22 (1H, dd, J=1.7, 8.2 Hz), 7.35 (1H, d, J=8.2 Hz), 7.59 (2H, d, J=8.5 Hz).

2-tert-Butyl-5-trimethylsilanylethvnyl 1-[(4'-nitro)phenoxy]benzene (Compound L)

Employing the same general procedure as for the preparation of 2-tert-butyl-5-trimethylsilanylethynyl-1-[(4'-trifluoromethyl)phenoxy]benzene (Compound K), 512 mg (2.2 mmol) of 5-bromo-2-tert-butylphenol (Compound H) was converted into crude 5-bromo-2-tert-butyl-1-[(4'-nitro)phenoxy]benzene using 490 mg (4.0 mmol) of potassium t-butoxide, 807 mg (4.2 mmol) of cuprous iodide, 463 mg (1.9 mmol) of 4-iodonitrobenzene and 5.5 mL of pyridine. Purification by flash chromatography (silica, 3% ethyl acetate in hexane) gave crude 5-bromo-2-tert-butyl-1-[(4'-nitro)phenoxy]benzene. The crude sample was converted into the title compound using 339 mg (0.5 mmol) of bis(triphenylphosphine)palladium (II) chloride, 91 mg (0.5 mmol) of cuprous iodide, 2.1 mL (1.9 g, 19.3 mmol) of trimethylsilyl acetylene and 7 mL of triethylamine. Purification by flash chromatography (preabsorbed onto silica with 100% chloroform, eluted with 2% ethyl acetate in hexane) gave the title compound as a yellow oil.

PMR (CDCl$_3$): δ 0.21 (9H, s), 1.34 (9H, s), 6.97 (1H, d, J=1.6 Hz), 6.99–7.04 (2H, m), 7.27 (1H, dd, J=1.6, 8.2 Hz), 7.38 (1H, d, J=8.2 Hz), 8.20–8.26 (2H, m).

2-tert-Butyl-5-ethynyl-1-[(4'-trifluoromethyl)phenoxy]benzene (Compound M)

To a solution of 177 mg (0.45 mmol) of trimethylsilanylethynyl-1-[(4'-trifluoromethyl)phenoxybenzene (Compound K) in 3 mL of methanol and 2 mL of dichloromethane (under a blanket of argon) was added 18.5 mg (0.1 mmol) of potassium carbonate. The yellow solution mixture was stirred at ambient temperature for 16 hours at which time 16 mg (0.1 mmol) of potassium carbonate and 2 mL of methanol were added. The reaction mixture was allowed to stir at ambient temperature for 3.5 hours, concentrated in vacuo, extracted between ethyl acetate and sat. NaHCO$_3$ (aq.) solution and the layers were separated. The organic phase was washed with brine, dried over MgSO$_4$, filtered and concentrated in vacuo to give the title compound as a yellow oil which was of sufficient purity to use without further purification.

PMR (CDCl$_3$): δ 1.36 (9H, s), 3.02 (1H, s), 6.96 (1H, d, J=1.6 Hz), 7.03 (2H, d, J=8.6 Hz), 7.24 (1H, dd, J 1.6, 8.2 Hz), 7.38 (1H, d, J=8.2 Hz), 7.59 (2H, d, J=8.6 Hz).

2-tert-Butyl-5-ethynyl-1-[(4'-nitro)phenoxy]benzene (Compound N)

Employing the same general procedure as for the preparation of 2-tert-butyl-5-ethynyl-1-[(4'-trifluoromethyl)phenoxy]benzene (Compound M), 403 mg (1.1 mmol) 2-ten-butyl-5-trimethylsilanylethynyl-1-[(4'-nitro)phenoxy]benzene (Compound L) was converted into the title compound using 38 mg (0.3 mmol) of potassium carbonate and 5 mL of methanol. Purification by flash chromatography (silica, 4% ethyl acetate in hexane) gave the title compound as a yellow oil which later solidified.

PMR (CDCl$_3$): δ 1.36 (9H, s), 3.06 (1H, s), 6.95–7.30 (3H, m), 7.30 (1H, dd, J=1.6, 8.2 Hz), 7.41 (1H, d, J=8.2 Hz), 8.20–8.26 (2H, m).

2-tert-Butyl-5-ethynyl-1-[(4'-carbomethoxy)phenoxy]benzene (Compound O)

Employing the same general procedure as for the preparation of 2-tert-butyl-5-trimethylsilanylethynyl-1-[(4'-trifluoromethyl)phenoxy]benzene (Compound K), 410 mg (1.8 mmol) of 5-bromo-2-tert-butylphenyl (Compound H) was converted into crude 5-bromo-2-tert-butyl-1-[(4'-carboethoxy)phenoxy]benzene using 207 mg (1.7 mmol) of potassium t-butoxide, 341 mg (1.8 mmol) of cuprous iodide, 260 (0.9 mmol) of ethyl 4-iodobenzoate and 6 mL of pyridine. Purification by flash chromatography (silica, 1% ethyl acetate in hexane) gave crude 5-bromo-2-tert-butyl-1-[(4'-carboethoxy)phenoxy]benzene. The crude sample was converted into 2-tert-butyl-5-trimethylsilanylethynyl-1-[(4'-carboethoxy)phenoxy]benzene using 77 mg (0.1 mmol) of bis(triphenylphosphine)palladium (II) chloride, 21 mg (0.1 mmol) of cuprous iodide, 0.5 mL (430 mg, 4.4 mmol) of trimethylsilyl acetylene and 5 mL of triethylamine. Purification by flash chromatography (preabsorbed onto silica with 100% chloroform, eluted with 3% ethyl acetate in hexane) gave crude 2-tert-butyl-5-trimethylsilanylethynyl-1-[(4'-carboethoxy)phenoxy]benzene as a yellow oil. The crude acetylene was converted into the title compound using 10 mg (0.07 mmol) of potassium carbonate and 3 mL of methanol as described in the preparation of 2-tert-butyl-5-ethynyl-1-[(4'-trifluoromethyl)phenoxy]benzene (Compound M). Purification by flash chromatography (silica, 1% ethyl acetate in hexane) gave the title compound as clear, slightly yellow oil.

PMR (CDCl$_3$): δ 1.36 (9H, s), 3.01 (1H, s), 3.90 (3H, s), 6.94–7.02 (3H, m), 7.23 (1H, dd, J=1.6, 8.2 Hz), 7.37 (1H, d, J=8.2 Hz), 7.98–8.04 (2H, m).

4-tert-Butyl-3-[(4'-trifluoromethyl)phenoxy]benzoic acid (Compound P)

To a cold solution (-78° C.) of crude 5-bromo-2-tert-butyl-1-[(4'-trifluoromethyl)phenoxy]benzene (intermediate obtained during the preparation of 2-tert-butyl-5-trimethylsilanylethynyl-1-[(4'-trifluoromethyl)phenoxy]benzene (Compound K)) in 12 mL of anhydrous THF was added 0.86 mL (1.5 mmol) of tert-butyllithium (1.7M in pentane). The solution was allowed to stir at −78° C. for 1 hour and then carbon dioxide was bubbled into the solution continuously for 1 hour at −78° C. The reaction was quenched with 10% HCl (aq.) solution, diluted with ethyl acetate and the layers were separated. The organic phase was washed with water and brine, dried over MgSO$_4$, filtered and concentrated in vacuo. Purification by flash chromatography (silica, 10% ethyl acetate in hexane followed by 50% ethyl acetate in hexane) gave the title compound as a white solid.

PMR (Acetone-d$_6$): δ 1.42 (9H, s), 7.22 (2H, d, J=8.5 Hz), 7.50 (1H, d, J=1.8 Hz), 7.62 (1H, d, J=8.3 Hz), 7.76 (2H, d, J=8.5 Hz), 7.66 (1H, d, J=8.5 Hz), 7.82 (1H, dd, J=1.8, 8.3 Hz).

Benzyl 4-hydroxybenzoate (Compound Q)

A neat solution of 18.6 mL (15 g, 118.8 mmol) of 1,3-diisopropylcarbodiimide and 60 mg (0.6 mmol) of cuprous chloride was placed under a blanket of argon and then cooled to 0° C. in an ice bath. To this reaction mixture was added dropwise (via syringe) 12.9 mL (13.5 g, 124.7 mmol) of benzyl alcohol. The resultant green reaction mixture was allowed to stir at 0° C. overnight, filtered through celite (rinsing with hexane) and the filtrate then Kugelrohr distilled (105° C., 2 mm Hg) to give 2-benzyl-1,3-diisopropyl isourea as a clear, colorless oil. To a solution of 650 mg (4.7 mmol) of 4-hydroxybenzoic acid in 20 mL of tetrahydrofuran was added 1.1 g (4.7 mmol) of 2-benzyl-1,3-diisopropyl isourea. The reaction mixture was allowed to stir at ambient temperature overnight, filtered (rinsing with tetrahydrofuran) and then concentrated in vacuo. Purification by flash chromatography (silica, 3 25% ethyl acetate in hexane) gave the title compound as a white solid.

PMR (CDCl$_3$): δ 5.22 (1H, s), 5.35 (2H, s), 6.87 (2H, d, J=8.8 Hz), 7.34–7.50 (5H, m), 8.01 (2H, d, J=8.8 Hz).

4-tert-Butyl-3-[(4'-methyl)phenoxy]benzoic Acid (Compound R)

Employing the same general procedure as for the preparation of 4-tert-butyl-3-(4'-trifluoromethyl)phenoxy] benzoic acid (Compound P), 1.02 g (3.2 mmol) of 5-bromo-2-tert-butyl-1-[(4'-methyl)phenoxy]benzene (Compound J) was converted into the title compound using 4.7 mL (8.0 mmol) of tert-butyllithium solution (1.7M in pentane) and 10 mL of tetrahydrofuran. Purification by flash chromatography (silica, 3% methanol in chloroform) gave the title compound as a creme solid.

PMR (CDCl$_3$): δ 1.45 (9H, s), 2.32 (3H, s), 4.35 (2H, q, J=7.1 Hz), 6.93 (2H, d, J=8.2 Hz), 7.22 (2H, d, J=8.2 Hz), 7.39 (1H, d, J=1.7 Hz), 7.54 (1H, d, J=8.2 Hz), 7.70 (1H, dd, J=1.7, 8.2 Hz).

5-Bromo-2-tert-butyl-1-[(2'-amino-4'-ethyl)phenoxy] benzene (Compound S)

Employing the same general procedure as for the preparation of 5-bromo-2-tert-butyl-1-[(2'-amino-4'-methyl) phenoxy]benzene (Compound I), 781 mg (3.4 mmol) of 5-bromo-2-tert-butylphenol (Compound H) was converted into crude 5-bromo-2-tert-butyl-1-[4'-ethyl-2'-nitro) phenoxy]benzene using 611 mg (5.0 mmol) of potassium t-butoxide, 1.0 g (5.25 mmol) of cuprous iodide, 770 mg (~2.78 mmol) of 1-bromo-4-ethyl-2-nitrobenzene (80% purity, obtained from the nitration of 1-bromo-4-ethylbenzene) and 10 mL of pyridine. Purification by flash chromatography (silica, 5% ethyl acetate in hexane) gave crude 5-bromo-2-tert-butyl-1-[(4'-methyl-2'-nitro)phenoxy] benzene as a yellow oil. 290 mg of this crude sample was converted into the title compound using a balloon filled with hydrogen, 31 mg of 10% Pd/C, 4 mL of acetonitrile and 1 mL of methanol. Purification by flash chromatography (silica, 2% ethyl acetate in hexane) gave the title compound as a yellow oil.

PMR (CDCl$_3$): δ 1.24 (3H, t, J=7.5 Hz), 1.44 (9H, s), 2.58 (2H, q, J==7.5 Hz), 3.72 (2H, br s), 6.57 (1H, dd, J=2.1, 8.2 Hz), 6.68–6.74 (2H, m), 6.81 (1H, d, J=2.1 Hz), 7.09 (1H, dd, J=2.1, 8.4 Hz), 7.22 (1H, d, J=8.4 Hz).

5-Bromo-2-tert-butyl-1-[(4'-ethyl)phenoxy]benzene (Compound T)

Employing the same general procedure as for the preparation of 5-bromo-2-tert-butyl-1-[(4'-methyl)phenoxy] benzene (Compound J), 70 mg (0.2 mmol) of 5-bromo-2-tert-butyl-1-[(2'-amino-4'-ethyl)phenoxy]benzene (Compound S) was converted into the title compound using 0.5 mL (470 mg, 4.0 mmol) of isoamyl nitrite, 0.5 mL of trifluoroacetic acid, 1.2 mL of ethanol and 0.3 mL of hypophosphorous acid. Purification by flash chromatography (silica, 1% ethyl acetate in hexane) gave the title compound as a clear, colorless oil. PMR (CDCl$_3$): δ 1.26 (3H, t, J=7.6 Hz), 1.41 (9H, s), 2.66 (2H, q, J==7.6 Hz), 6.89–6.95 (3H, m), 7.13 (1H, dd, J=2.0, 8.4 Hz), 7.19 (2H, d, J=8.6 Hz), 7.24 (1H, d, J=8.4 Hz).

2-tert-Butyl-5-trimethylsilanylethynyl-1-[(4'-methyl) phenoxy]benzene (Compound U)

In a sealed tube vessel, a solution of 323 mg (1.0 mmol) of 5-bromo-2-tert-butyl-1-[(4'-methyl)phenoxy]benzene (Compound J) in 6 mL of triethylamine was sparged (with a stream of argon bubbled vigorously into the solution) for several minutes. To this solution was added 48 mg (0.25 mmol) of cuprous iodide and the resultant mixture was sparged with argon for several minutes. To this reaction mixture was then added 175 mg (0.25 mmol) of bis (triphenylphosphine)palladium(II) chloride. After sparging with argon for a couple of minutes, 1.1 mL (1.0 g, 10.1 mmol) of trimethylsilyl acetylene was added to the reaction mixture. The pressure tube was then sealed and heated in an oil bath (75° C.) for 3 days at which time an additional 178 mg (0.25 mmol) of bis(triphenylphosphine)palladium(II) chloride and 1.0 mL (0.9 g, 9.4 mmol) of trimethylsilyl acetylene were added. The reaction mixture was heated at 75° C. for 4 days, filtered through celite and washed with ethyl ether (100 mL). The filtrate was extracted with water (3×75 mL-portions) and brine, dried over MgSO$_4$, filtered and concentrated in vacuo to give a dark brown oil residue. Purification by flash chromatography (preabsorbed onto silica with 100% chloroform, eluted with 100% hexane) gave the title compound as a clear, colorless oil which solidified to a white solid.

PMR (CDCl$_3$): δ 0.19 (9H, s), 1.39 (9H, s), 2.34 (3H, s), 6.84–6.91 (3H, m), 7.10–7.17 (3H, m), 7.29 (1H, d, J=8.1 Hz).

2-tert-Butyl-5-trimethylsilanylethvnyl-1-[(4'-ethyl) phenoxy]benzene (Compound V)

Employing the same general procedure as for the preparation of 2-tert-butyl-5-trimethylsilanylethynyl-1-[(4'-methyl)phenoxy]benzene (Compound U), 52 mg (0.16 mmol) 5-bromo-2-tert-butyl-1-[(4'-ethyl)phenoxy]benzene (Compound T) was converted into the title compound using 28 mg (0.04 mmol) of bis(triphenylphosphine)palladium (II) chloride, 7 mg (0.04 mmol) of cuprous iodide, 0.2 mL (150 mg, 1.5 mmol) of trimethylsilyl acetylene and 3 mL of triethylamine. An additional 28 mg (0.04 mmol) of bis (triphenylphosphine)palladium (II) chloride, and 0.2 mL (150 mg, 1.5 mmol) of trimethylsilyl acetylene were added after 3 days of heating, and the resultant mixture was then heated at 75° C. for 4 more days. Purification by flash chromatography (preabsorbed onto silica with 100% chloroform, eluted with 100% hexane) gave the title compound as a yellow oil.

PMR (CDCl$_3$): δ 0.19 (9H, s), 1.25 (3H, t, J=7.6 Hz), 1.40 (9H, s), 2.64 (2H, q, J=7.6 Hz), 6.86–6.92 (3H, m), 7.12 (1H, dd, J=1.7, 8.1 Hz), 7.17 (1H, d, J=8.4 Hz), 7.29 (1H, d, J=8.1 Hz).

2-tert-Butyl-5-ethynyl-1-[(4'-methyl)phenoxy]benzene (Compound W)

Employing the same general procedure as for the preparation of 2-tert-butyl-5-ethynyl-1-[(4'-trifluoromethyl) phenoxy]benzene (Compound M), 280 mg (1.1 mmol) 2-tert-butyl-5-trimethylsilanylethynyl-1-[(4'-methyl) phenoxy]benzene (Compound U) was converted into the title compound using 29 mg (0.2 mmol) of potassium carbonate, 5 mL of methanol and 2 mL of dichloromethane. Purification by flash chromatography (silica, 100% ethyl acetate in hexane) gave the title compound as a slightly yellow oil.

PMR (CDCl$_3$): δ 1.41 (9H, s), 2.34 (3H, s), 2.97 (1H, s), 6.85–6.92 (3H, m), 7.12–7.18 (3H, m), 7.32 (1H, d, J=8.1 Hz).

2-tert-Butyl-5-ethynyl-1-[(4'-ethyl)phenoxy]benzene (Compound X)

Employing the same general procedure as for the preparation of 2-tert-butyl-5-ethynyl-1-[(4'-methyl)phenoxy] benzene (Compound W), 40 mg (0.1 mmol) 2-tert-butyl-5-trimethylsilanylethynyl-1-[(4'-ethyl)phenoxy]benzene (Compound V) was converted into the title compound using 4.3 mg (0.03 mmol) of potassium carbonate, 3 mL of methanol and 1 mL of dichloromethane. Purification by flash chromatography (silica, 100% hexane) gave the title compound as a clear, yellow oil.

PMR (CDCl$_3$): δ 0.19 (9H, s), 1.25 (3H, t, J=7.6 Hz), 1.40 (9H, s), 2.64 (2H, q, J=7.6 Hz), 6.86–6.92 (3H, m), 7.12 (1H, dd, J=1.7, 8.1 Hz), 7.17 (1H, d, J=8.4 Hz), 7.29 (1H, d, J=8.1 Hz).

2-tert-Butyl-5-trimethylsilanylethynyl-1-[(4'-methyl-2'-nitro)phenoxy]benzene (Compound Y)

Employing the same general procedure as for the preparation of 2-tert-butyl-5-trimethylsilanylethynyl-1-[(4'-trifluoromethyl)phenoxy]benzene (Compound K), 4.0 g (17.5 mmol) of 5-bromo-2-tert-butylphenol (Compound H) was converted into crude 5-bromo-2-tert-butyl-1-[(4'-methyl-2'-nitro)phenoxy]benzene using 3.85 g (31.5 mmol) of potassium t-butoxide, 6.35 g (33.5 mmol) of cuprous iodide, 3.25 g (21.0 mmol) of 4-fluoro-3-nitrotoluene and 53 mL of pyridine. Purification by flash chromatography (silica, 1% ethyl acetate in hexane) gave crude 5-bromo-2-tert-butyl-1-[(4'-methyl-2'-nitro)phenoxy]benzene. 1.87 g (5.1 mmol) of this crude sample was converted into the title compound using 898 mg (1.3 mmol) of bis(triphenylphosphine)palladium (II) chloride, 246 mg (1.3 mmol) of cuprous iodide, 5.5 mL (5.1 g, 51.6 mmol) of trimethylsilyl acetylene and 11 mL of triethylamine. Purification by flash chromatography (preabsorbed onto silica with 100% chloroform, eluted with 1% ethyl acetate in hexane) gave the title compound as a brown semisolid.

PMR (CDCl$_3$): δ 0.20 (9H, s), 1.39 (9H, s), 2.40 (3H, s), 6.82 (1H, d, J=8.4 Hz), 6.86 (1H, d, J=1.7 Hz), 7.20 (1H, dd, J=1.7, 8.2 Hz), 7.31 21 (1H, dd, J=2.1, 8.4 Hz), 7.34 (1H, d, J=8.2 Hz), 7.78 (1H, d, J=2.1 22 Hz).

2-tert-Butyl-5-ethynyl-1-[(4'-methyl-2'-nitro)phenoxy]benzene (Compound Z)

Employing the same general procedure as for the preparation of 2-tert-butyl-5-ethynyl-1-[(4'-methyl)phenoxy]benzene (Compound W), 1.7 g (4.35 mmol) of 2-tert-butyl-5-trimethylsilanylethynyl-1-[(4'-methyl-2'-nitro)phenoxy]benzene (Compound Y) was converted into the title compound using 150 mg (1.1 mmol) of potassium carbonate, 25 mL of methanol and 2.5 mL of dichloromethane. Purification by flash chromatography (silica, 5% ethyl acetate in hexane) gave the title compound as a yellow oil.

PMR (CDCl$_3$): δ 1.40 (9H, s), 2.41 (3H, s), 3.01 (1H, s), 6.84 (1H, d, J=8.8 Hz), 6.87 (1H, d, J=1.7 Hz), 7.22 (1H, dd, J=1.7, 8.2 Hz), 7.32 (1H, dd, J=2.1, 8.8 Hz), 7.37 (1H, d, J=8.2 Hz), 7.78 (1H, d, J=2.1 Hz).

Ethyl 4-[[4'-tert-butyl-3'-(4"-trifluoromethyl)phenoxy]phenylethynyl]benzoate (Compound 1)

A solution of 47 mg (0.15 mmol) of 2-tert-butyl-5-ethynyl-1-[(4'-trifluoromethyl)phenoxy]benzene (Compound M) in 2.5 mL of triethylamine was sparged (by having a stream of argon bubbled vigorously into the solution) for several minutes. To this solution was added a solution of 46 mg (0.2 mmol) of ethyl 4-iodobenzoate (Compound A) in 0.5 mL of triethylamine. After sparging with argon for several minutes, 8.5 mg (0.04 mmol) of cuprous iodide was added to the solution and the resultant mixture was cooled to 0° C. in an ice bath and then sparged with argon for a couple of minutes. To this mixture was added 30 mg (0.04 mmol) of bis(triphenylphosphine)palladium (II) chloride. The reaction mixture was stirred at 0° C. for 8 minutes (initial 2 minutes performed under sparging conditions), allowed to warm to ambient temperature and then stirred at ambient temperature for 24 hours. The reaction mixture was filtered through celite, washed with ethyl ether (250 mL) and the collected filtrate washed with brine (twice), dried over MgSO$_4$, filtered and concentrated in vacuo to a solid residue. Purification by flash chromatography (silica, 2% ethyl acetate in hexane) gave the title compound as a white solid.

PMR (CDCl$_3$): δ 1.37–1.45 (12H, m), 4.38 (2H, q, J=7.1 Hz), 7.02 (1H, d, J=1.6 Hz), 7.06 (2H, d, J=8.5 Hz), 7.30 (1H, dd, J=1.6, 8.2 Hz), 7.43 (1H, d, J=8.2 Hz), 7.53 (2H, d, J=8.5 Hz), 7.61 (2H, d, J=8.9 Hz), 8.00 (2H, d, J=8.5 Hz).

Ethyl 4-[[4'-tert-butyl-3'-(4'-trifluomethyl)phenoxy]phenylethynyl]-2-fluoro-benzoate (Compound 2)

Employing the same general procedure as for the preparation of ethyl 4-[[4'-tert-butyl-3'-(4'-trifluoromethyl)phenoxy]phenylethynyl]benzoate (Compound 1), 46 mg (0.15 mmol) of 2-tert-butyl-5-ethynyl-1-[(4'-trifluoromethyl)phenoxy]benzene (Compound M) was converted into the title compound using 45.5 mg (0.2 mmol) of ethyl 2-fluoro-4-iodobenzoate (Compound C), 28 mg (0.04 mmol) of bis(triphenylphosphine)palladium (II) chloride, 8 mg (0.04 mmol) of cuprous iodide and 3 mL of triethylamine. Purification by flash chromatography (silica, 1% ethyl acetate in hexane) gave the title compound as a yellow solid.

PMR (CDCl$_3$): δ 1.39 (3H, t, J=7.1 Hz), 1.40 (9H, s), 4.39 (2H, q, J=7.1 Hz), 7.01 (1H, d, J=1.6 Hz), 7.06 (2H, d, J=8.5 Hz), 7.23 (1H, dd, J=1.6, J (C—F)=11.2 Hz), 7.29 (2H, d, J=1.6, 8.2 Hz), 7.43 (1H, d, J=8.2 Hz), 7.61 (2H, d, J=8.9 Hz), 7.89 (1H, t, J=7.9 Hz, J (C—F)=7.8).

4-[[4'-tert-Butyl-3'-(4"-trifluoromethyl)phenoxy]phenylethynyl]benzoic Acid (Compound 3)

To a solution of 33 mg (0.07 mmol) of 4-[[4'-tert-butyl-3'-(4"-trifluoromethyl)phenoxy]phenylethynyl]benzoate (Compound 1) in 2.8 mL of ethanol and 0.5 mL of tetrahydrofuran was added 0.7 mL (0.7 mmol) of NaOH solution (1M in water). The reaction mixture was allowed to stir at ambient temperature for 22 hours, concentrated in vacuo, cooled to 0° C. in an ice bath and acidified with 1N H$_2$SO$_4$ (aq.) solution. The solution was extracted between ethyl ether and brine and the organic phase was separated. The organic phase was dried over MgSO$_4$, filtered and concentrated in vacuo to, and the residue was recrystallized from methanol to give the title compound as a white solid. PMR (Acetone-d$_6$): δ 1.41 (9H, s), 7.12 (1H, d, J=1.8 Hz), 7.22 (2H, d, J=8.8 Hz), 7.39 (1H, dd, J=1.8, 8.2 Hz), 7.55 (1H, d, J=8.2 Hz), 7.63 (2H, d, J=8.4 Hz), 7.77 (2H, d, J=8.9 Hz), 8.03 (2H, d, J=8.4 Hz).

4-[[4'-tert-Butyl-3'-(4"-trifluoromethyl)phenoxy]phenylethynyl]-2-fluoro-benzoic Acid (Compound 4)

Employing the same general procedure as for the preparation of 4-[[4'-tert-butyl-3'-(4"-trifluoromethyl)phenoxy]phenylethynyl]benzoic acid (Compound 3), 40 mg (0.085 mmol) of ethyl 4-[[4'-tert-butyl-3'-(4"-trifluoromethyl)phenoxy]phenylethynyl]-2-fluoro-benzoate (Compound 2) was converted into the title compound using 0.8 mL (0.8 mmol) of NaOH solution (1M in water), 3.2 mL of ethanol and 0.5 mL of. tetrahydrofuran. Recrystallization from methanol gave the title compound as yellow crystals.

PMR (Aceton-d$_6$): δ 1.41 (9H, s), 7.13 (1H, d, J=1.7 Hz), 7.22 (2H, d, J=8.8 Hz), 7.38 (1H, dd, J=1.4, J (C—F)=7.0 Hz), 7.40–7.45 (2H, m), 7.56 (1H, d, J=8.2 Hz), 7.77 (2H, d, J=8.6 Hz), 7.96 (1H, t, J=7.9 Hz, J (C—F)=7.9).

Ethyl 6-[[4'-tert-butyl-3'-(4"-trifluomethyl)phenoxy]phenylethnyl]-3-nicotinoate (Compound 5)

Employing the same general procedure as for the preparation of ethyl 4-[[4'-tert-butyl-3'-(4'-trifluoromethyl)phenoxy]phenylethynyl]benzoate (Compound 1), 50 mg (0.15 mmol) of 2-tert-butyl-5-ethynyl-1-[(4'- trifluoromethyl)phenoxy]benzene (Compound M) was converted into the title compound using 45 mg (0.2 mmol) of ethyl 6-iodo-3-nicotinoate (Compound G), 28 mg (0.04 mmol) of bis(triphenylphosphine)palladium (II) chloride, 8 mg (0.04 mmol) of cuprous iodide and 3 mL of triethylamine. Purification by flash chromatography (silica, 5% ethyl acetate in hexane) gave the title compound as a clear, colorless oil.

PMR (CDCl$_3$): δ 1.38–1.44 (12H, m), 4.42 (2H, q, J=7.1 Hz), 7.04–7.10 (3H, m), 7.36 (1H, dd, J=1.7, 8.2 Hz), 7.45 (1H, d, J=8.2 Hz), 7.54 (1H, d, J=8.4 Hz), 7.61 (2H, d, J=8.7 Hz), 8.26 (1H, dd, J=2.0, 8.2 Hz), 9.17 (1H, d, J=2.0 Hz).

6-[[4'-tert-Butyl-3'-(4"-trifluomethyl)phenoxy]phenylethynyl]-3-nicotinic Acid (Compound 6)

Employing the same general procedure as for the preparation of 4-[[4'-tert-butyl-3'-(4"-trifluoromethyl)phenoxy]phenylethynyl]benzoic acid (Compound 3), 42 mg (0.09 mmol) of ethyl 6-[[4'-tert-butyl-3'-(4"-trifluoromethyl)phenoxy]phenylethynyl]-3-nicotinoate (Compound 5) was converted into the title compound using 0.9 mL (0.9 mmol) of NaOH solution (1M in water), 3.5 mL of ethanol and 0.5 mL of tetrahydrofuran. Recrystallization from methanol gave the title compound as slightly yellow crystals.

PMR (CDCl$_3$): δ 1.40 (9H, s), 7.04–7.12 (3H, m), 7.36 (1H, dd, J=1.6, 8.2 Hz), 7.44 (1H, d, J=8.2 Hz), 7.53 (1H, d, J=8.2 Hz), 7.61 (2H, d, J=8.6 Hz), 8.29 (1H, dd, J=2.0, 8.2 Hz), 9.17 (1H, d, J=2.0 Hz).

Ethyl 4-[[4'-tert-butyl-3'-(4"-nitro)phenoxy]phenylethynyl]-2-fluorobenzoate (Compound 7)

Employing the same general procedure as for the preparation of ethyl 4-[[4'-tert-butyl-3'-(4"-trifluoromethyl)phenoxy]phenylethynyl]benzoate (Compound 1), 236 mg (0.8 mmol) of 2-tert-butyl-5-ethynyl-1-[(4'-nitro)phenoxy]benzene (Compound N) was converted into the title compound using 236 mg (0.8 mmol) of ethyl 2-fluoro-4-iodobenzoate (Compound C), 140 mg (0.2 mmol) of bis(triphenylphosphine)palladium (II) chloride, 39 mg (0.2 mmol) of cuprous iodide and 7 mL of triethylamine. Purification by flash chromatography (silica, 1–3% ethyl acetate in hexane) gave the title compound as a white solid.

PMR (CDCl$_3$): δ 1.38 (9H, s), 1.40 (3H, t, J=7.1 Hz), 4.39 (2H, q, J=7.1 Hz), 7.03–7.08 (3H, m), 7.24 (1H, dd, J=1.4, J (C—F)=10.2 Hz), 7.29 (1H, dd, J=1.5, 8.2 Hz), 7.34 (1H, dd, J=1.8, 8.2 Hz), 7.47 (1H, d, J=8.2 Hz), 7.89 (1H, t, J=7.9 Hz, J (C—F)=7.8 Hz), 8.22–8.28 (2H, m).

Ethyl 4-[[4'-tert-Butyl-3'-(4"-amino)phenoxy]phenylethynyl]-2-fluorobenzoate (Compound 8)

To a solution of 178 mg (0.4 mmol) of ethyl 4-[[4'-tert-butyl-3'-(4"-nitro)phenoxy]phenylethynyl]-2-fluoro-benzoate (Compound 7) in 10 mL of tetrahydrofuran was added 2 mL of glacial acetic acid and 2 mL of water. To the resultant reaction mixture was added 2.9 mL (4.3 mmol) of titanium (III) chloride solution (19 wt % in 20 wt % HCl). The purple reaction mixture was allowed to stir at ambient temperature for 2 days, extracted between ethyl acetate and water. The layers were separated and the aqueous phase was washed with ethyl acetate (twice). The organic phases were combined and washed with sat. NHCO$_3$ (aq.) solution, water and brine, dried over MgSO$_4$, filtered and concentrated in vacuo to a yellow-brown oil. To remove residual acetic acid generated during the workup, the oil was further extracted between ethyl ether and sat. NHCO$_3$ (aq.) solution. The layers were separated and the organic phase was washed with brine, dried over MgSO$_4$, filtered and concentrated in vacuo to a yellow solid. Purification by flash chromatography (silica, 25–40% ethyl acetate in hexane) gave the title compound as a white solid.

PMR (CDCl$_3$): δ 1.39 (3H, t, J=7.1 Hz), 1.45 (9H, s), 3.60 (2H, br s), 4.39 (2H, q, J=7.1 Hz), 6.69–6.74 (2H, m), 6.82–6.88 (3H, m), 7.14 (1H, dd, J=1.6, 8.2 Hz), 7.22 (1H, dd, J=1.6 Hz, J (C—F)=11.3 Hz), 7.27 (1H, dd, J=2.7, 8.2 Hz), 7.34 (1H, d, J=8.2 Hz), 7.87 (1H, t, J=7.9 Hz, J (C—F)=7.8 Hz).

Trimethylsilanylethyl 4-[[4'-tert-butyl-3'-(4"-carbomethoxy)phenoxy]phenylethynyl]benzoate (Compound 9)

Employing the same general procedure as for the preparation of ethyl 4-[[4'-tert-butyl-3'-(4"-trifluoromethyl)phenoxy]phenylethynyl]benzoate (Compound 1), 48 mg (0.2 mmol) of 2-tert-butyl-5-ethynyl-1-[(4'-carbomethoxy)phenoxy]benzene (Compound 0) was converted into the title compound using 62 mg (0.2 mmol) of trimethylsilanylethyl 2-fluoro-4-iodobenzoate (Compound D), 27 mg (0.04 mmol) of bis(triphenylphosphine)palladium (II) chloride, 7 mg (0.04 mmol) of cuprous iodide and 3 mL of triethylamine. Purification by flash chromatography (silica, 1% ethyl acetate in hexane) gave the title compound as a slightly yellow oil.

PMR (CDCl$_3$): δ 0.08 (9H, s), 1.14 (2H, dd, J=8.4, 10.3 Hz), 1.40 (9H, s), 3.91 (3H, s), 4.42 (2H, dd, J=8.4, 10.3 Hz), 7.00–7.04 (3H, m), 7.23 (1H, dd, J=~2 Hz, J (C—F)=~10 Hz), 7.25–7.30 (2H, m), 7.43 (1H, d, J=8.2 Hz), 7.88 (1H, t, J=7.8 Hz, J (C—F)=7.8 Hz), 8.02–8.08 (2H, m).

4-[[4'-tert-Butyl-3'-(4"-carbomethoxy)phenoxy]phenylethynyl]-2-fluorobenzoic Acid (Compound 10)

To a solution of 43 mg (0.08 mmol) of trimethylsilanyl-ethyl 4-[[4'-tert-butyl-3'-(4"-carbomethoxy)phenoxy]phenylethynyl]-2-fluorobenzoate (Compound 9) in 2 mL of tetrahydrofuran was added 0.1 mL (0.1 mmol) of tetrabutylammonium fluoride (1M in tetrahydrofuran). The slightly yellow solution was allowed to stir at ambient temperature for 30 minutes, quenched with 0.5 mL of 10% HCl (aq.) solution, extracted between ethyl acetate and water, and the layers separated. The organic phase was washed with brine, dried over MgSO$_4$, filtered and concentrated in vacuo to a yellow oil. To remove residual tetrabutylammonium hydroxide, the oil was further extracted between ethyl acetate and 10% HCl (aq.) solution and the layers separated. The organic phase was washed with 10% HCl (aq.) solution (twice) and brine, dried over MgSO$_4$, filtered and concentrated in vacuo to give the title compound as an off-white solid.

PMR (Acetone-d$_6$): δ 1.40 (9H, s), 3.87 (3H, s), 7.08–7.14 (3H, m), 7.35–7.39 (3H, m), 7.56 (1H, d, J=8.2 Hz), 7.95 (1H, t, J=8.0 Hz, J (C—F)=7.6 Hz), 8.03–8.10 (2H, m).

4-[[4'-tert-Butyl-3'-(4"-nitro)phenoxy]phenylethynyl]-2-fluoro-benzoic Acid (Compound 11)

To a solution of 24 mg (0.05 mmol) of ethyl 4-[[4'-tert-butyl-3'-(4"-nitro)phenoxy]phenylethynyl]-2-fluorobenzoate (Compound 7) in 2 mL of tetrahydrofuran was added 0.5 mL (0.5 mmol) of LiOH solution (1M in water). The reaction mixture was allowed to stir at ambient temperature for 2 days, concentrated in vacuo, and extracted between hexane and water. The layers were separated and the aqueous phase was diluted with ethyl ether, cooled to 0° C. in an ice bath and acidified with 1N H$_2$SO$_4$ (aq.) solution. The solution was diluted with brine and the organic phase was separated. The organic phase was dried over MgSO$_4$, filtered and concentrated in vacuo to give the title compound as a white solid.

PMR (Acetone-d$_6$): 1.40 (9H, s), 7.20–7.26 (3H, m), 7.35–7.48 (3H, m), 7.60 (1H, d, J=8.2 Hz), 7.96 (1H, t, J=7.9 Hz, J (C—F)=7.9 Hz), 8.29–8.36 (2H, m).

Ethyl 4-[[4'-tert-butyl-3'-(4"-trifluoromethyl)phenoxy]benzoylamino]-2-fluoro-benzoate (Compound 12)

A solution of 125 mg (0.4 mmol) of 4-tert-butyl-3-[(4'-trifluoromethyl)phenoxy]benzoic acid (Compound P) in 3 mL of thionyl chloride was refluxed (85° C.) for 1 hour and then concentrated in vacuo. To the crude acid chloride obtained was added a solution of 67.5 mg (0.4 mmol) of crude ethyl 4-amino-2-fluorobenzoate (Compound E) in dichloromethane followed by excess pyridine. The reaction mixture was allowed to stir at ambient temperature for 2 hours, concentrated in vacuo and extracted between ethyl acetate and sat. NaHCO$_3$ (aq.) solution. The layers were separated and the organic phase was washed with water and brine, dried over MgSO$_4$, filtered and concentrated in vacuo. Purification by flash chromatography (silica, 10% ethyl acetate in hexane followed by 50% ethyl acetate in hexane) gave the title compound as a white solid.

PMR (CDCl$_3$): δ 1.40 (3H, t, J=7.1 Hz), 1.44 (9H, s), 4.38 (2H, q, J=7.1 Hz), 7.07 (2H, d, J=8.5 Hz), 7.25–7.30 (2H, m), 7.40 (1H, br s), 7.55–7.65 (3H, m), 7.71 (1H, dd, J=2 Hz, J(C—F)=10.7 Hz), 7.86 (1H, br s), 7.94 (1H, t, J(C—F)=8.4 Hz).

4-[[4'-tert-Butyl-3'-(4"-trifluoromethyl)phenoxy]benzoylamino]-2-fluorobenzoic Acid (Compound 13)

To a solution of 113 mg (0.2 mmol) of crude ethyl 4-[[4'-tert-butyl-3'-(4"-trifluoromethyl)phenoxy]benzoylamino]-2-fluoro-benzoate (Compound 12) in 3 mL of ethanol was added 2 mL of NaOH (aq.) solution. The reaction mixture was allowed to stir at ambient temperature for 4 days, acidified to pH=1 with 10% HCl (aq.) solution, and concentrated in vacuo. The residue was extracted with ethyl acetate and the layers were separated. The organic layer was washed with sat. NaHCO$_3$ (aq.) solution and brine, dried over MgSO$_4$, filtered and concentrated in vacuo to a white solid. Recrystallization from acetonitrile gave the title compound as white crystals.

PMR (Acetone-d$_6$): δ 1.42 (9H, s), 7.21 (2H, d, J=8.6 Hz), 7.54 (1H, dd, J=2.0, 8.5 Hz), 7.60 (1H, d, J=2.0 Hz), 7.66 (1H, d, J=8.5 Hz), 7.75 (2H, d, J=-8.6 Hz) 7.82–7.95 (3H, m), 9.88 (1H, br s).

Ethyl 4-[[4'-tert-butyl-3'-(4"-methyl)phenoxy]phenylvinyl]benzoate (Compound 14)

In a sealed tube vessel was added a solution of 8 mg (0.045 mmol) of ethyl 4-vinylbenzoate (Compound F) in 1 mL of triethylamine. This solution was degassed (by having a stream of argon bubbled vigorously into the solution) for 5 minutes and then a solution of 8 mg (0.03 mmol) of 5-bromo-2-tert-butyl-1-[(4'-methyl)phenoxy]benzene (Compound J) in 1 mL of triethylamine was added. The clear, colorless solution was degassed for 5 minutes and then approximately 1 mg of palladium (II) acetate was added followed by approximately 2 mg of tri-(o-tolyl)phosphine. The tube was sealed and then heated at 95° C. for 15.5 hours, cooled to ambient temperature and extracted between ethyl ether and water. The layers were separated and the organic phase was washed with water and brine, dried over MgSO$_4$, filtered and concentrated in vacuo to a yellow residue. Purification by flash chromatography (silica, 1% ethyl acetate in hexane) gave the title compound as a white solid.

PMR (CDCl$_3$): δ 1.39 (3H, t, J=7.1 Hz), 1.43 (9H, s), 2.35 (3H, s), 4.37 (2H, q, J=7.1 Hz), 6.91 (2H, d, J=8.5 Hz), 6.95 (1H, d, J=16.1 Hz), 6.96 (1H, d, J=1.8 Hz), 7.06 (1H, d, J=16.1 Hz), 7.16 (2H, d, J=8.2 Hz), 7.21 (1H, d, J=1.8, 8.2 Hz), 7.39 (1H, d, J=8.2 Hz), 7.49 (2H, d, J=8.5 Hz), 7.99 (2H, d, J=8.5 Hz). 4-[[4'-tert-Butyl-3'-(4"-methyl)phenoxy]phenylvinyl]benzoic Acid (Compound 15)

Employing the same general procedure as for the preparation of 4-[[4'-tert-butyl-3'-(4"-nitro)phenoxy]phenylethynyl]-2-fluoro-benzoic acid (Compound 11), 8 mg (0.02 mmol) of ethyl 4-[[4'-tert-butyl-3'-(4"-methyl)phenoxy]phenylvinyl]benzoate (Compound 14) was converted into the title compound (white solid) using 0.3 mL (0.3 mmol) of LiOH solution (1M in water) and 1.0 mL of tetrahydrofuran. Rinsing of the white solid obtained with 10% ethyl acetate in hexane gave the title compound.

PMR (Acetone-d$_6$): δ 1.41 (9H, s), 2.32 (3H, s), 6.91 (2H, d, J=8.2 Hz), 7.04 (1H, d, J=1.7 Hz), 7.18 (1H, d, J=16.5 Hz), 7.20 (2H, d, J=8.2 Hz), 7.32 (1H, d, J=16.5 Hz), 7.37 (1H, dd, J=1.7, 8.2 Hz), 7.44 (1H, d, J=8.2 Hz), 7.67 (2H, d, J=8.4 Hz) 7.98 (2H, d, J=8.4 Hz).

Ethyl 4-[[4'-tert-butyl-3'-(4"-azido)phenoxy]phenylethynyl]-2-fluoro-benzoate (Compound 16)

To a cold solution (0° C.) of 73.8 mg (0.17 mmol) of ethyl 4-[[4'-tert-butyl-3'-(4"-amino)phenoxy]phenylethynyl]-2-fluoro-benzoate (Compound 8) in 3 mL of ethanol was added 0.5 mL of trifluoroacetic acid followed by 0.5 mL (0.4 g, 3.72 mmol) of isoamyl nitrite. The resultant solution was allowed to stir at 0° C. for 2 hours and then a solution of 12 mg (0.18 mmol) of sodium azide in 0.2 mL of water was added. The yellow solution immediately turned orange in color. The ice bath was removed and the reaction mixture was allowed to warm to ambient temperature where it was stirred for 18 hours and then concentrated in vacuo. Purification by flash chromatography (silica, 1.5% ethyl acetate in hexane) gave the title compound as a clear oil.

PMR (CDCl$_3$): δ 1.39 (3H, t, J=7.2 Hz), 1.42 (9H, s), 4.35 (2H, q, J=7.1 Hz), 6.86–6.92 (2H, m), 7.03 (1H, d, J=1.7 Hz), 7.34 (1H, dd, J=1.7, 8.2 Hz), 7.38 (1H, dd, J=1.6 Hz, J(C—F)=10.7 Hz), 7.41 (1H, dd, J=1.6, 8.4 Hz), 7.52 (1H, d, J=8.2 Hz), 7.73–7.80 (2H, m), 7.92 (1H, dd, J=8.1 Hz, J(C—F)=7.8 Hz). 4-[[4'-tert-Butyl-3'-(4"-azido)phenoxy]phenylethynyl]-2-fluoro-benzoic Acid (Compound 17)

Employing the same general procedure as for the preparation of 4-[[4'-tert-butyl-3'-(4"-trifluoromethyl)phenoxy]phenylethynyl]benzoic acid (Compound 3), 65 mg (0.14 mmol) of ethyl 4-[[4'-tert-butyl-3'-(4"-azido)phenoxy]phenylethynyl]-2-fluoro-benzoate (Compound 16) was converted into the title compound using 1.4 mL (1.4 mmol) of NaOH solution (1M in water), 5.6 mL of ethanol and 0.5 mL of tetrahydrofuran. Recrystallization from ethyl acetate/hexane gave the title compound as yellow crystals. PMR (Acetone-d$_6$): δ 1.43 (9H, s), 6.96 (1H, d, J=1.6 Hz), 7.08–7.19 (4H, m), 7.18 (1H, dd, J=1.6, 8.2 Hz), 7.35–7.43 (2H, m), 7.51 (2H, d, J=8.2 Hz), 7.95 (1H, dd, J=7.9 Hz, J(C—F)=7.6 Hz).

Ethyl 4-[[4'-tert-butyl-3'-(4"-iodo)phenoxy]phenylethynyl]-2-fluoro-benzoate (Compound 18) and ethyl 4-[[4'-tert-butyl-3'-phenoxy]phenylethynyl]-2-fluoro-benzoate (Compound 19)

Employing the same general procedure as for the preparation of ethyl 4-[[4'-tert-butyl-3'-(4"-azido)phenoxy]phenylethynyl]benzoic acid (Compound 16), 70 mg (0.2 mmol) of ethyl 4-[[4'-tert-butyl-3'-(4"-amino)phenoxy]phenylethynyl]-2-fluoro-benzoate (Compound 8) was converted into the title compounds using 0.04 mL (0.3 mmol) of isoamyl nitrite, 2.0 mL of ethanol, 0.1 mL of trifluoroacetic acid and a solution of 100 mg (0.7 mmol) of sodium iodide in 0.5 mL of water. The reaction proceeded slowly and required additional amounts of isoamyl nitrite and sodium iodide in water (bringing to a total the amounts listed above). Purification by flash chromatography (silica, 1% ethyl acetate in hexane) followed by HPLC separation (Partisil 10 PAC, 1% ethyl acetate in hexane) gave the title compounds as a clear, colorless oil (Compound 18, RT=49 minutes) and as a white solid (Compound 19, RT=47 minutes), respectively.

Ethyl 4-[[4'-tert-butyl-3'-(4"-iodo)phenoxy]phenylethynyl]-2-fluoro-benzoate (Compound 18): PMR (CDCl$_3$): δ 1.39 (3H, t, J=7.2 Hz), 1.42 (9H, s), 4.35 (2H, q, J=7.1 Hz), 6.86–6.92 (2H, m), 7.03 (1H, d, J=1.7 Hz), 7.34 (1H, dd, J=1.7, 8.2 Hz), 7.38 (1H, dd, J=1.6 Hz, J (C—F)=10.7 Hz), 7.41 (1H, dd, J=1.6, 8.4 Hz), 7.52 (1H, d, J=8.2 Hz), 7.73–7.80 (2H, m), 7.92 (1H, dd, J=8.1 Hz, J (C—F)=7.8 Hz).

Ethyl 4-[[4'-tert-butyl-3'-phenoxy]phenylethynyl]-2-fluoro-benzoate (Compound 19): PMR (CDCl$_3$): δ 1.39 (3H, t, J=7.1 Hz), 1.43 (9H, s), 4.39 (2H, q, J=7.1 Hz), 6.96 (1H, d, J=1.6 Hz), 6.97–7.04 (2H, m), 7.09–7.16 (1H, m), 7.19–7.30 (3H, m), 7.34–7.42 (3H, m), 7.87 (1H, dd, J=7.9 Hz, J (C—F)=7.8 Hz).

4-[[4'-tert-Butyl-3'-(4"-iodo)phenoxy]phenylethynyl]-2-fluoro-benzoic Acid (Compound 20)

Employing the same general procedure as for the preparation of 4-[[4'-tert-butyl-3'-(4"-trifluoromethyl)phenoxy]phenylethynyl]benzoic acid (Compound 3), 9 mg (0.02 mmol) of ethyl 4-[[4'-tert-butyl-3'-(4"-iodo)phenoxy]phenylethynyl]-2-fluoro-benzoate (Compound 18) was converted into the title compound (white solid) using 0.25 mL (0.25 mmol) of NaOH solution (1M in water), 1.5 mL of ethanol and 0.3 mL of tetrahydrofuran. Rinsing of the white solid obtained with 1% ethyl acetate in hexane gave the title compound.

PMR (Acetone-d$_6$): δ 1.40 (9H, s), 6.86–6.92 (2H, m), 7.03 (1H, d, J=1.6 Hz), 7.30–7.44 (3H, m), 7.52 (1H, d, J=8.2 Hz), 7.73–7.78 (2H, m), 7.94 (1H, dd, J=7.9 Hz, J (C—F)=7.7 Hz).

Ethyl 4-[[4'-tert-butyl-3'-(4"-trifluoromethyl)phenoxy]phenylvinyl]benzoate (Compound 21)

Employing the same general procedure as for the preparation of ethyl 4-[[4'-tert-butyl-3'-(4"-methyl)phenoxy]phenylvinyl]benzoate (Compound 14), 56 mg (0.15 mmol) of 2-tert-butyl-5-bromo-1-[(4'-trifluoromethyl)phenoxy]benzene (intermediate used in the preparation of 2-tert-butyl-5-trinethylsilanylethynyl-1-[(4'-trifluoromethyl)phenoxy]benzene (Compound K)) was converted into the title compound using 1.8 mg (0.008 mmol) of palladium (II) acetate, 4.8 mg (0.016 mmol) of tri-(o-tolyl)phosphine, 45.5 mg (0.3 mmol) of ethyl 4-vinyl benzoate (Compound F) and 2 mL of triethylamine. Purification by flash chromatography (silica, 1% ethyl acetate in hexane) gave the title compound as a clear oil which solidified upon standing to a white solid.

PMR (CDCl$_3$): δ 1.37–1.42 (12H, m), 4.37 (2H, q, J=7.1 Hz), 6.95–7.15 (5H, m), 7.30 (1H, dd, J=1.8, 8.3 Hz), 7.45 (1H, d, J=8.3 Hz), 7.51 (2H, d, J=8.4 Hz), 7.60 (2H, d, J=9.0 Hz), 8.00 (2H, d, J=8.4 Hz).

4-[[4'-tert-Butyl-3'-(4"-trifluoromethyl)phenoxy]vinyl]benzoic Acid (Compound 22)

Employing the same general procedure as for the preparation of 4-[[4'-tert-butyl-3'-(4"-nitro)phenoxy]phenylethynyl]-2-fluoro-benzoic acid (Compound 11), 37 mg (0.08 mmol) of ethyl 4-[[4'-tert-butyl-3'-(4"-trifluoromethyl)phenoxy]phenylvinyl]benzoate (Compound 21) was converted into the title compound using 0.8 mL (0.8 mmol) of LiOH solution (1M in water) and 3 mL of tetrahydrofuran. Recrystallization from acetonitrile/tetrahydrofuran gave the title compound as white crystals.

PMR (Acetone-d$_6$): δ 1.38 (9H, s), 7.18 (2H, d, J=8.7 Hz), 7.23 (1H, d, J=1.6 Hz), 7.27 (1H, d, J=16.5 Hz), 7.37 (1H, d, J=16.5 Hz), 7.48 (1H, dd, J=1.7, 8.2 Hz), 7.52 (1H, d, J=8.2 Hz), 7.67 (2H, d, J=8.4 Hz), 7.73 (2H, d, J=8.7 Hz), 7.98 (2H, d, J=8.4 Hz).

Ethyl 4-[[4'-tert-butyl-3'-(4"-methyl)phenoxy]phenylethynyl]-2-fluoro-benzoate (Compound 23)

Employing the same general procedure as for the preparation of ethyl 4-[[4'-tert-butyl-3'-(4"-trifluoromethyl)phenoxy]phenylethynyl]benzoate (Compound 1), 208.5 mg (0.8 mmol) of 2-tert-butyl-5-ethynyl-1-[(4'-methyl)phenoxy]benzene (Compound W) was converted into the title compound using 231.5 mg (0.8 mmol) of ethyl 2-fluoro-4-iodobenzoate (Compound C), 139 mg (0.2 mmol) of bis(triphenylphosphine)palladium (II) chloride, 38 mg (0.2 mmol) of cuprous iodide and 6 mL of triethylamine. Purification by flash chromatography (preabsorbed onto silica with 100% chloroform, eluted with 1.5% ethyl acetate in hexane) gave the title compound as a yellow solid. PMR (CDCl$_3$): δ 1.40 (3H, t, J=7.1 Hz), 1.44 (9H, s), 2.36 (3H, s), 4.39 (2H, q, J=7.1 Hz), 6.92 (2H, d, 8.5 Hz), 6.95 (1H, d, J=1.7 Hz), 7.17 (2H, d, J=8.5 Hz), 7.19 (1H, dd, J=1.7, 8.2 Hz), 7.22 (1H, dd, J=1.5, J (C—F)=7.9 Hz), 7.27 (1H, dd, J=1.5, 8.2 Hz), 7.38 (1H, d, J=8.2 Hz), 7.88 (1H, dd, J=7.9 Hz, J (C—F)=7.8 Hz).

Ethyl 4-[[4'-tert-butyl-3'-(4"-ethyl)phenoxy]phenylethynyl]-2-fluoro-benzoate (Compound 24)

Employing the same general procedure as for the preparation of ethyl 4-[[4'-tert-butyl-3'-(4"-trifluoromethyl)phenoxy]phenylethynyl]benzoate (Compound 1), 28 mg (0.1 mmol) of 2-tert-butyl-5-ethynyl-1-[(4'-ethyl)phenoxy]benzene (Compound X) was converted into the title compound using 32 mg (0.1 mmol) of ethyl 2-fluoro-4-iodobenzoate (Compound C), 18 mg (0.03 mmol) of bis(triphenylphosphine)palladium (II) chloride, 5 mg (0.03 mmol) of cuprous iodide and 3 mL of triethylamine. Purification by flash chromatography (preabsorbed onto silica with 100% chloroform, eluted with 0–1.5% ethyl acetate in hexane) gave the title compound as a slightly yellow solid.

PMR (CDCl$_3$): δ 1.26 (3H, t, J=7.6 Hz), 1.39 (3H, t, J=7.1 Hz), 1.43 (9H, s), 2.64 (2H, q, J=7.6 Hz), 4.39 (2H, q, J=7.1 Hz), 6.93 (2H, d, 8.6 Hz), 6.95 (1H, d, J=1.6 Hz), 7.17–7.30 (5H, m), 7.37 (1H, d, J=8.2 Hz), 7.87 (1H, dd, J=7.8 Hz, J (C—F)=7.7 Hz).

4-[[4'-tert-Butyl-3'-(4"-ethyl)phenoxy]phenylethynyl]-2-fluoro-benzoic Acid (Compound 25)

Employing the same general procedure as for the preparation of 4-[[4'-tert-butyl-3'-(4"-nitro)phenoxy]phenylethynyl]-2-fluoro-benzoic acid (Compound 11), 32 mg (0.07 mmol) of ethyl 4-[[4'-tert-butyl-3'-(4"-ethyl)phenoxy]phenylvinyl]-2-fluoro-benzoate (Compound 24) was converted into the title compound using 0.7 mL (0.7 mmol) of LiOH solution (1M in water) and 3 mL of tetrahydrofuran. Recrystallization from acetonitrile/tetrahydrofuran gave the title compound as slightly yellow prisms.

PMR (Acetone-d$_6$): δ 1.22 (3H, t, J=7.4 Hz), 1.43 (9H, s), 2.64 (2H, q, J=7.4), 6.92 (1H, d, 1.7 Hz), 6.96 (2H, d, J=8.5 Hz), 7.23–7.35 (3H, m), 7.34–7.52 (2H, m), 7.48 (1H, d, J=8.2 Hz), 7.93 (1H, dd, J=8.0 Hz, J (C—F)=7.5 Hz).

4-[[4'-tert-Butyl-3'-(4"-methyl)phenoxy]phenylethynyl]-2-fluoro-benzoic Acid (Compound 26)

Employing the same general procedure as for the preparation of 4-[[4'-tert-butyl-3'-(4"-nitro)phenoxy]phenylethynyl]-2-fluoro-benzoic acid (Compound 11), 207.5 mg (0.5 mmol) of ethyl 4-[[4'-tert-butyl-3'-(4"-methyl)phenoxy]phenylethynyl]-2-fluoro-benzoate (Compound 23) was converted into the title compound using 4.8 mL (4.8 mmol) of LiOH solution (1M in water) and 19 mL of tetrahydrofuran. Recrystallization from acetonitrile/tetrahydrofuran gave the title compound as white crystals.

PMR (Acetone-$d_6$): δ 1.43 (9H, s), 2.33 (3H, s), 6.91 (1H, d, 1.7 Hz), 6.94 (2H, d, J=8.5 Hz), 7.24 (2H, d, J=8.5 Hz), 7.27 (1H, dd, J=1.7, 8.2 Hz), 7.37 (1H, dd, J=1.5, J (C—F)=10.9 Hz), 7.40 (1H, dd, J=1.5, 8.0 Hz), 7.48 (1H, d, J=8.2 Hz), 7.94 (1H, dd, J=8.0 Hz, J (C—F)=7.5 Hz).

Ethyl 4-[[4'-tert-butyl-3'-(4'-methyl-2"-nitro)phenoxy]phenylethynyl]benzoate (Compound 27)

Employing the same general procedure as for the preparation of ethyl 4-[[4'-tert-butyl-3'-(4'-trifluoromethyl)phenoxy]phenylethynyl]benzoate (Compound 1), 1.04 g (3.4 mmol) of 2-tert-butyl-5-ethynyl-1-[(4'-methyl-2'-nitro)phenoxy]benzene (Compound Z) was converted into the title compound using 930 mg (3.4 mmol) of ethyl 4-iodobenzoate (Compound A), 590 mg (0.8 mmol) of bis(triphenylphosphine)palladium (II) chloride, 170 mg (0.9 mmol) of cuprous iodide and 17 mL of triethylamine. Purification by flash chromatography (preabsorbed onto silica with 100% chloroform, eluted with 5% ethyl acetate in hexane) gave the title compound as a yellow solid.

PMR (CDCl$_3$): δ 1.39 (3H, t, J=7.1 Hz), 1.43 (9H, s), 2.41 (3H, s), 4.38 (2H, q, J=7.1 Hz), 6.88 (2H, d, 8.5 Hz), 6.92 (1H, d, J=1.6 Hz), 7.28 (1H, dd, J=1.6, 8.2 Hz), 7.34 (1H, dd, J=2.0, 8.5 Hz), 7.41 (1H, d, J=8.2 Hz), 7.52 (2H, d, J=8.3 Hz), 7.79 (1H, d, J=2.0 Hz), 7.99 (2H, d, J=8.3 Hz).

Ethyl 4-[[4'-tert-butyl-3'-(2"-amino-4"-methyl)phenoxy]phenylethynyl]benzoate (Compound 28)

Employing the same general procedure as for the preparation of ethyl 4-[[4'-tert-butyl-3'-(4"-amino)phenoxy]phenylethynyl]-2-fluoro-benzoate (Compound 8), 1.18 g (2.6 mmol) of ethyl 4-[[4'-tert-butyl-3'-(4"-methyl-2"-nitro)phenoxy]phenylethynyl]benzoate (Compound 27) was converted into the title compound using 100 mL of tetrahydrofuran, 20 mL of glacial acetic acid, 20 mL of water and 17.5 mL (25.7 mmol) of titanium (III) chloride solution (19 wt % in 20 wt % HCl). Purification by flash chromatography (silica, 10% ethyl acetate in hexane) gave the title compound as a white solid.

PMR (CDCl$_3$): δ 1.39 (3H, t, J=7.1 Hz), 1.48 (9H, s), 2.29 (3H, s), 3.75 (2H, s), 4.37 (2H, q, J=7.1 Hz), 6.55 (1H, dd, J=1.8, 8.2 Hz), 6.68–6.73 (3H, m), 6.87 (1H, d, 1.8 Hz), 7.17 (1H, dd, J=1.6, 8.0 Hz), 7.36 (1H, d, J=8.0 Hz), 7.52 (2H, d, J=8.5 Hz), 7.98 (2H, d, J=8.5 Hz).

Ethyl 4-[[4'-tert-butyl-3'-(4"-methyl)phenoxy]phenylethnynl]benzoate (Compound 29)

Employing the same general procedure as for the preparation of 5-bromo-2-tert-butyl-1-[(4'-methyl)phenoxy]benzene (Compound J), 947 mg (2.2 mmol) of ethyl 4-[[4'-tert-butyl-3'-(2"-amino-4"-methyl)phenoxy]phenylethynyl]benzoate (Compound 28) was converted into the title compound using 6 mL (5.2 g, 44.7 mmol) of isoamyl nitrite, 7.5 mL of trifluoroacetic acid, 15 mL of ethanol and 3.5 mL of hypophosphorous acid. Purification by flash chromatography (silica, 1–3% ethyl acetate in hexane) gave the title compound as a white solid. PMR (CDCl$_3$): δ 1.39 (3H, t, J=7.1 Hz), 1.43 (9H, s), 2.35 (3H, s), 4.37 (2H, q, J=7.1 Hz), 6.91 (2H, d, 8.7 Hz), 6.95 (1H, d, J=1.7 Hz), 7.16 (2H, d, J=8.7 Hz), 7.19 (1H, dd, J=1.7, 8.1 Hz), 7.36 (1H, d, J=8.1 Hz), 7.51 (2H, d, J=8.6 Hz), 7.98 (2H, d, J=8.6 Hz).

4-[[4'-tert-Butyl-3'-(4"-methyl)phenoxy]phenylethynyl]benzoic Acid (Compound 30)

Employing the same general procedure as for the preparation of 4-[[4'-tert-butyl-3'-(4"-trifluoromethyl)phenoxy]phenylethynyl]benzoic acid (Compound 3), 700 mg (1.7 mmol) of ethyl 4-[[4'-tert-butyl-3'-(4"-methyl)phenoxy]phenylethynyl]benzoate (Compound 29) was converted into the title compound using 17.5 mL (17.5 mmol) of NaOH solution (1M in water), 50 mL of ethanol and 10 mL of tetrahydrofuran. Recrystallization from acetonitrile/tetrahydrofuran gave the title compound as white crystals.

PMR (DMSO-$d_6$): δ 1.38 (9H, s), 2.29 (3H, s), 6.84 (1H, d, J=1.6 Hz), 6.91 (2H, d, J=8.4 Hz), 7.22 (2H, d, J=8.4 Hz), 7.28 (1H, dd, J=1.6, 8.2 Hz), 7.44 (1H, d, J=8.2 Hz), 7.61 (2H, d, J=8.3 Hz), 7.91 (2H, d, J=8.3 Hz).

4-[[4'-tert-Butyl-3'-(4"-methyl-2"-nitro)phenoxy]phenylethynyl]benzoic Acid (Compound 31)

Employing the same general procedure as for the preparation of 4-[[4'-tert-butyl-3'-(4"-trifluoromethyl)phenoxy]phenylethynyl]benzoic acid (Compound 3), 50 mg (0.1 mmol) of ethyl 4-[[4'-tert-butyl-3'-(4"-methyl-2"-nitro)phenoxy]phenylethynyl]benzoate (Compound 27) was converted into the title compound using 1.1 mL (1.1 mmol) of NaOH solution (1M in water), 4.4 mL of ethanol and 0.5 mL of tetrahydrofuran. Recrystallization from acetonitrile/tetrahydrofuran gave the title compound as yellow crystals.

PMR (Acetone-$d_6$): δ 1.43 (9H, s), 2.44 (3H, s), 7.01 (1H, d, J=1.6 Hz), 7.04 (1H, d, J=8.6 Hz), 7.35 (1H, dd, J=1.6, 8.2 Hz), 7.52 (1H, d, J=8.2 Hz), 7.54 (1H, dd, J=1.8, 8.6 Hz), 7.61 (2H, d, J=8.2 Hz), 7.88 (1H, d, J=1.8 Hz), 8.02 (2H, d, J=8.2 Hz).

4-[[4'-ten-Butyl-3'-(2"-amino-4"-methyl)phenoxy]phenylethynyl]benzoic Acid (Compound 32)

Employing the same general procedure as for the preparation of 4-[[4'-tert-butyl-3'-(4"-trifluoromethyl)phenoxy]phenylethynyl]benzoic acid (Compound 3), 22 mg (0.05 mmol) of ethyl 4-[[4'-tert-butyl-3'-(2"-amino-4"-methyl)phenoxy]phenylethynyl]benzoate (Compound 28) was converted into the title compound using 0.5 mL (0.5 mmol) of NaOH solution (1M in water), 2.5 mL of ethanol and 0.3 mL of tetrahydrofuran. Recrystallization from acetonitrile gave the title compound as yellow crystals.

PMR (Acetone-$d_6$): δ 1.49 (9H, s), 2.23 (3H, s), 2.81 (2H, br s), 6.48 (1H, dd, J=2.2, 8.5 Hz), 6.68 (1H, d, J=8.2 Hz), 6.75 (1H, d, J=2.2 Hz), 6.78 (1H, d, J=1.7 Hz), 7.20 (1H, dd, J=1.7, 8.2 Hz), 7.43 (1H, d, J=8.2 Hz), 7.60 (2H, d, J=8.5 Hz), 8.01 (2H, d, J=8.5 Hz).

Benzyl 4-[[4'-tert-butyl-3'-(4"-methyl)phenoxy]benzoyloxy]benzoate (Compound 33)

Employing the same general procedure as for the preparation of trimethylsilanylethyl 2-fluoro-4-iodobenzoate (Compound D), 60.5 mg (0.2 mmol) of 4-tert-butyl-3-[(4'-methyl)phenoxy]benzoic acid (Compound R) was converted into the title compound using 45 mg (0.2 mmol) of 1-(3-dimethylaminopropyl-3-ethyl carbodiimide hydrochloride), 27.5 mg (0.2 mmol) of 4-dimethylaminopyridine, 7.5 mL of dichloromethane and 48 mg (0.2 mmol) of benzyl 4-hydroxybenzoate (Compound Q). Purification by flash chromatography (silica, 1% ethyl acetate in hexane) gave the title compound as a clear, colorless oil.

PMR (CDCl$_3$): δ 1.46 (9H, s), 2.33 (3H, s), 5.36 (2H, s), 6.90 (2H, d, J=8.4 Hz), 7.15 (2H, d, J=8.4 Hz), 7.19–7.25 (3H, m), 7.30–7.48 (5H, m), 7.52 (1H, d, J=8.2, 7.58 (1H, d, J=1.8 Hz), 7.84 (1H, dd, J=1.8, 8.2 Hz), 8.12 (2H, d, J=8.7 Hz).

4-[[4'-tert-Butyl-3'-(4"-methyl)phenoxy]benzoyloxy]benzoic Acid (Compound 34)

To a solution of benzyl 4-[[4'-tert-butyl-3'-(4"-methyl)phenoxy]benzoyloxy]benzoate (Compound 33) in 5 mL of ethyl acetate (degassed with argon) was added 7 mg of 10% Pd/C. The reaction mixture was placed under a hydrogen balloon for 23 hours, filtered through celite, and washed with ethyl acetate. The filtrate obtained was concentrated in vacuo to give the title compound as a white solid.

PMR (DMSO-$d_6$): δ 1.42 (9H, s), 2.49 (3H, s), 6.94 (2H, d, J=8.5 Hz), 7.22 (2H, d, J=8.5 Hz), 7.34 (2H, d, J=8.6 Hz), 7.37 (1H, d, J=1.9 Hz), 7.62 (1H, d, J=8.2 Hz), 7.83 (1H, dd, J=1.9, 8.2 Hz) 7.99 (2H, d, J=8.6 Hz).

Ethyl 4-[[4'-tert-butyl-3'-(4"-methyl)phenoxy]benzoylamino]-2-fluoro-benzoate (Compound 35)

Employing the same general procedure as for the preparation of ethyl 4-[[4'-tert-butyl-3'-(4"-trifluoromethyl)phenoxy]benzoylamino]-2-fluoro-benzoate (Compound 12), 62 mg (0.2 mmol) of 4-tert-butyl-3-[(4'-methyl)phenoxy]benzoic acid (Compound R) was converted into the title compound using 2 mL of thionyl chloride followed by 42 mg (0.2 mmol, 90% purity) of ethyl 4-amino-2-fluorobenzoate (Compound E), 5 mL of dichloromethane and 1 mL of pyridine. Purification by flash chromatography (silica, 10–20% ethyl acetate in hexane) gave the title compound as a clear, colorless oil.

PMR (CDCl$_3$): 1.39 (3H, t, J=7.1 Hz), 1.46 (9H, s), 2.34 (3H, s), 4.37 (2H, q, J=7.1 Hz), 6.90 (2H, d, 8.5 Hz), 7.17 (2H, d, J=8.5 Hz), 7.23 (1H, dd, J=1.7, 8.4 Hz), 7.28 (1H, d, J=1.8 Hz), 7.45 (1H, dd, J=1.8, 8.2 Hz), 7.51 (1H, d, J=8.2 Hz), 7.70 (1H, dd, J=2.1 Hz, J (C—F)=12.9 Hz), 7.80 (1H, br s), 7.92 (1H, dd, J=8.4 Hz, J (C—F)=8.3 Hz).

4-[[4'-tert-Butyl-3'-(4"-methyl)phenoxy]benzoylamino]-2-fluoro-benzoic acid (Compound 36)

Employing the same general procedure as for the preparation of 4-[[4'-tert-butyl-3'-(4"-trifluoromethyl)phenoxy]phenylethynyl]benzoic acid (Compound 3), 37.5 mg (0.08 mmol) of ethyl 4-[[4'-tert-butyl-3'-(4'-methyl)phenoxy]benzoylamino]-2-fluoro-benzoate (Compound 35) was converted into the title compound using 0.8 mL (0.8 mmol) of NaOH solution (1M in water), 3.2 mL of ethanol and 0.4 mL of tetrahydrofuran.

PMR (Acetone-$d_6$): 1.44 (9H, s), 2.31 (3H, s), 6.90 (2H, d, 8.4 Hz), 7.21 (2H, d, J=8.4 Hz), 7.44 (1H, d, J=1.5 Hz), 7.50–7.60 (2H, m), 7.68–7.74 (1H, m), 7.87 (1H, dd, J=1.7 Hz, J (C—F)=13.6 Hz), 7.91 (1H, dd, J=8.4 Hz, J (C—F)= 8.6 Hz), 9.85 (1H, br s).

What is claimed is:

1. A process of activating a retinoid receptor or binding to said retinoid receptor in a mammal in need thereof wherein said activating or binding to a retinoid receptor has a beneficial therapeutic effect, the process comprising the step of administering to said mammal an effective amount of a compound of the formula

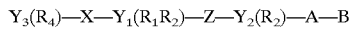

$$Y_3(R_4)-X-Y_1(R_1R_2)-Z-Y_2(R_2)-A-B$$

where $Y_1$ is phenyl or naphthyl, said phenyl or naphthyl groups being substituted with an $R_1$ group, and further substituted or unsubstituted with one or two $R_2$ groups;

$R_1$ is $C_{1-10}$alkyl, 1-adamantyl, 2-tetrahydropyranoxy, trialkylsilanyloxy where alkyl has up to 6 carbons, OH, alkoxy where the alkyl group has up to 10 carbons, alkylthio where the alkyl group has up to 10 carbons, or $OCH_2OC_{1-6}$alkyl;

$R_2$ is lower alkyl of 1 to 6 carbons, F, Cl, Br, I, $CF_3$, $CF_2CF_3$, OH, $OR_3$, $NO_2$, $N(R_3)_2$, CN, $N_3$, $COR_3$, or $NHCOR_3$, COOH, $COOR_3$;

X is S, SO, $SO_2$, or O;

Z is —C≡C—,
—N=N—,
—N(O)=N—,
—N=N(O)—,
—N=CR$_3$—,
—CR$_3$=N,
—(CR$_3$=CR$_3$)$_n$— where n is an integer having the value 0–5,
—CO—NR$_3$—,
—CS—NR$_3$—,
—NR$_3$—CO,
—NR$_3$—CS,
—COO—,
—OCO—;
—CSO—;
—OCS—;
—CO—CR$_3$=CR$_3$—;

$R_3$ is independently H or lower alkyl of 1 to 6 carbons;

$V_2$ is a phenyl or naphthyl group, said pheny or naphthyl groups being unsubstituted or substituted with one or two $R_2$ groups, or when Z is —(CR$_3$=CR$_3$)$_n$ and n is 3, 4 or 5 then $Y_2$ represents a direct valence bond between said (CR$_3$=CR$_3$)$_n$ group and B;

$Y_3$ is pheny or naphthyl, said pheny or naphthyl groups being unsubstituted or substituted with one to three $R_4$ groups, where $R_4$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, F, Cl, Br, I, $NO_2$, CN, $NR_3$, $N_3$, COOH, $COOC_{1-6}$alkyl; OH, SH, $OC_{1-6}$alkyl, $SC_{1-6}$alkyl;

A is $(CH_2)_q$ where q is 0–5, and

B is COOH or $COOR_8$, where $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, or a pharmaceutically acceptable salt of said compound.

2. A process in accordance with claim 1 where $Y_1$ is phenyl unsubstituted or substituted with up to two $R_2$ groups.

3. A process in accordance with claim 1 where $Y_2$ is phenyl unsubstituted or substituted with up to two $R_2$ groups.

4. A process in accordance with claim 1 where X is O.

5. A process in accordance with claim 1 where X is S.

6. A process in accordance with claim 1 where Z is selected from the group consisting of —C≡C—, —CH=CH—, —CONH—, —COO—, —OCO—, —NHCO—, and —(CR$_3$=CR$_3$)$_n$— where n is zero or 3.

7. A process in accordance with claim 6 where Z is selected from the group consisting of —C≡C—, —C=C—, —COO— and —CONH—.

8. A process in accordance with claim 1 where $R_1$ is branch chained alkyl.

9. A process in accordance with claim 1 where the compound used in the process has the formula
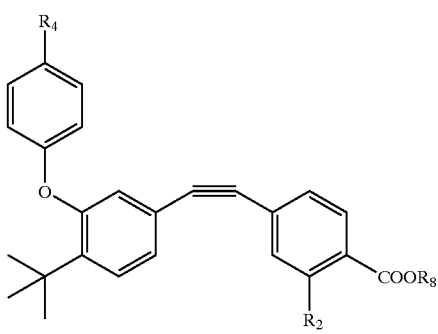
where $R_2$ is H or F, and $R_4$ is alkyl of 1 to 10 carbons.
10. A process in accordance with claim 9 where the compound used in the process has the formula
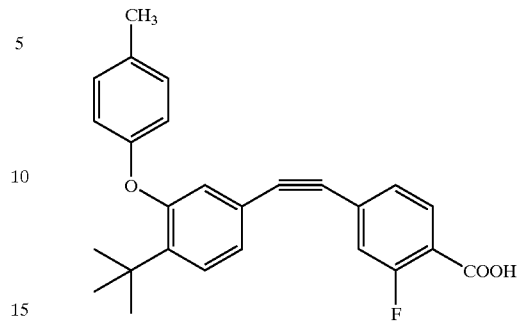
* * * * *